(12) United States Patent
Palmer et al.

(10) Patent No.: US 9,861,413 B2
(45) Date of Patent: Jan. 9, 2018

(54) SCREWS FOR GENERATING AND APPLYING COMPRESSION WITHIN A BODY

(71) Applicant: Arthrex, Inc., Naples, FL (US)

(72) Inventors: Matthew Palmer, Cambridge, MA (US); Robert Devaney, Billerica, MA (US); Ragheb El Khaja, Billerica, MA (US); Andrew Sennett, Billerica, MA (US); Matthew Fonte, Concord, MA (US)

(73) Assignee: Arthrex, Inc., Naples, FL (US)

( * ) Notice: Subject to any disclaimer, the term of this patent is extended or adjusted under 35 U.S.C. 154(b) by 437 days.

(21) Appl. No.: 14/539,650

(22) Filed: Nov. 12, 2014

(65) Prior Publication Data

US 2015/0134014 A1    May 14, 2015

Related U.S. Application Data

(60) Provisional application No. 61/902,338, filed on Nov. 11, 2013, provisional application No. 61/903,820, filed on Nov. 13, 2013.

(51) Int. Cl.
*A61B 17/86* (2006.01)
*A61B 17/88* (2006.01)

(52) U.S. Cl.
CPC .......... *A61B 17/864* (2013.01); *A61B 17/863* (2013.01); *A61B 17/8685* (2013.01); *A61B 17/8875* (2013.01); *A61B 17/8894* (2013.01)

(58) Field of Classification Search
CPC ................ A61B 17/864; A61B 17/866; A61B 2017/681
See application file for complete search history.

(56) References Cited

U.S. PATENT DOCUMENTS

| 2,580,821 A | 1/1952 | Nicola |
| 3,960,147 A | 6/1976 | Murray |
| 4,175,555 A | 11/1979 | Herbert |

(Continued)

FOREIGN PATENT DOCUMENTS

| EP | 0826340 A2 | 3/2008 |
| FR | 2787313 A1 | 6/2000 |

(Continued)

OTHER PUBLICATIONS

Huang et al., Ion release from NiTi orthodontic wires in artificial saliva with various acidities, Biomaterials, 24, 2003, 3585-3592.

(Continued)

*Primary Examiner* — Andrew Yang
(74) *Attorney, Agent, or Firm* — Carlson, Gaskey & Olds, P.C.

(57) ABSTRACT

A compression screw system, said compression screw system comprising:
a compression screw comprising a shaft, a screw thread formed on said shaft at a distal location, and a bone-engaging feature formed on said shaft at a proximal location, wherein at least a portion of said shaft disposed between said screw thread and said bone-engaging feature is capable of being stretched; and
a holding element connectable to said compression screw for releasably holding said at least a portion of said shaft in a stretched condition.

34 Claims, 20 Drawing Sheets

(56) References Cited

U.S. PATENT DOCUMENTS

| | | |
|---|---|---|
| 4,428,376 A | 1/1984 | Mericle |
| 4,444,181 A | 4/1984 | Wevers et al. |
| 4,503,569 A | 3/1985 | Dotter |
| 4,512,338 A | 4/1985 | Balko et al. |
| 4,570,623 A | 2/1986 | Ellison et al. |
| 4,733,665 A | 3/1988 | Palmaz |
| 4,858,601 A | 8/1989 | Glisson |
| 4,905,679 A | 3/1990 | Morgan |
| 4,922,905 A | 5/1990 | Strecker |
| 4,950,227 A | 8/1990 | Savin et al. |
| 4,959,064 A | 9/1990 | Engelhardt |
| 4,959,065 A | 9/1990 | Arnett et al. |
| 5,026,390 A | 6/1991 | Brown |
| 5,044,540 A | 9/1991 | Dulebohn |
| 5,061,275 A | 10/1991 | Wallstén et al. |
| 5,089,006 A | 2/1992 | Stiles |
| 5,098,434 A | 3/1992 | Serbousek |
| 5,246,443 A | 9/1993 | Mai |
| 5,474,557 A | 12/1995 | Mai |
| 5,607,530 A | 3/1997 | Hall et al. |
| 5,680,981 A | 10/1997 | Mililli et al. |
| 5,766,218 A | 6/1998 | Arnott |
| 5,779,707 A | 7/1998 | Bertholet et al. |
| 5,876,434 A | 3/1999 | Flomenblit et al. |
| 5,947,999 A | 9/1999 | Groiso |
| 6,030,162 A | 2/2000 | Huebner |
| 6,048,344 A | 4/2000 | Schenk |
| 6,187,009 B1 | 2/2001 | Herzog et al. |
| 6,306,140 B1 | 10/2001 | Siddiqui |
| 6,325,805 B1 | 12/2001 | Ogilvie et al. |
| 6,533,157 B1 | 3/2003 | Whitman |
| 6,569,173 B1 | 5/2003 | Blatter et al. |
| 6,607,530 B1 | 8/2003 | Carl et al. |
| 6,623,486 B1 | 9/2003 | Weaver et al. |
| 6,656,184 B1 | 12/2003 | White et al. |
| 6,685,708 B2 | 2/2004 | Monassevitch et al. |
| 6,761,731 B2 | 7/2004 | Majercak |
| 6,773,437 B2 | 8/2004 | Ogilvie et al. |
| 7,175,626 B2 * | 2/2007 | Neff ............ A61B 17/7225 606/86 A |
| 7,229,452 B2 | 6/2007 | Kayan |
| 7,481,832 B1 | 1/2009 | Meridew et al. |
| 7,582,107 B2 | 9/2009 | Trail et al. |
| 7,618,441 B2 | 11/2009 | Groiso |
| 7,625,395 B2 | 12/2009 | Mückter |
| 7,794,483 B2 | 9/2010 | Capanni |
| 7,875,070 B2 | 1/2011 | Molaei |
| 7,955,388 B2 | 6/2011 | Jensen et al. |
| 7,976,648 B1 | 7/2011 | Boylan et al. |
| 7,985,222 B2 | 7/2011 | Gall et al. |
| 7,993,380 B2 | 8/2011 | Hawkes |
| 8,048,134 B2 | 11/2011 | Partin |
| 8,080,044 B2 | 12/2011 | Biedermann et al. |
| 8,114,141 B2 | 2/2012 | Appenzeller et al. |
| 8,118,952 B2 | 2/2012 | Gall et al. |
| 8,137,351 B2 | 3/2012 | Prandi |
| 8,216,398 B2 | 7/2012 | Bledsoe et al. |
| 8,221,478 B2 | 7/2012 | Patterson et al. |
| 8,393,517 B2 | 3/2013 | Milo |
| 8,425,588 B2 | 4/2013 | Molaei |
| 8,486,121 B2 | 7/2013 | Biedermann et al. |
| 8,584,853 B2 | 11/2013 | Knight et al. |
| 8,597,337 B2 | 12/2013 | Champagne |
| 8,721,646 B2 | 5/2014 | Fox |
| 8,790,379 B2 | 7/2014 | Bottlang et al. |
| 8,801,732 B2 | 8/2014 | Harris et al. |
| 8,808,294 B2 | 8/2014 | Fox et al. |
| 8,864,804 B2 | 10/2014 | Champagne et al. |
| 9,017,331 B2 | 4/2015 | Fox |
| 9,095,338 B2 | 8/2015 | Taylor et al. |
| 9,101,349 B2 | 8/2015 | Knight et al. |
| 9,204,932 B2 | 12/2015 | Knight et al. |
| 9,326,804 B2 | 5/2016 | Biedermann et al. |
| 9,339,268 B2 | 5/2016 | Fox |
| 9,408,647 B2 | 8/2016 | Cheney |
| 9,451,955 B2 | 9/2016 | Fox |
| 9,451,957 B2 | 9/2016 | Fox |
| 2002/0058940 A1 | 5/2002 | Frigg et al. |
| 2002/0111641 A1 | 8/2002 | Peterson et al. |
| 2002/0198527 A1 | 12/2002 | Muckter |
| 2004/0111089 A1 | 6/2004 | Stevens et al. |
| 2004/0230193 A1 | 11/2004 | Cheung et al. |
| 2004/0260377 A1 | 12/2004 | Flomenblit et al. |
| 2005/0043757 A1 | 2/2005 | Arad et al. |
| 2005/0096660 A1 | 5/2005 | Allen |
| 2005/0152770 A1 | 7/2005 | Tschakaloff et al. |
| 2005/0277940 A1 | 12/2005 | Neff |
| 2005/0288707 A1 | 12/2005 | De Canniere et al. |
| 2006/0264954 A1 | 11/2006 | Sweeney, II et al. |
| 2007/0233124 A1 | 10/2007 | Corrao et al. |
| 2007/0260248 A1 | 11/2007 | Tipirneni |
| 2007/0265631 A1 | 11/2007 | Fox |
| 2007/0270855 A1 | 11/2007 | Partin |
| 2008/0065154 A1 | 3/2008 | Allard et al. |
| 2008/0071373 A1 | 3/2008 | Molz et al. |
| 2008/0132894 A1 | 6/2008 | Coilard-Lavirotte et al. |
| 2008/0234763 A1 | 9/2008 | Patterson et al. |
| 2008/0249574 A1 | 10/2008 | McCombs et al. |
| 2009/0018556 A1 | 1/2009 | Prandi |
| 2009/0105768 A1 | 4/2009 | Cragg et al. |
| 2009/0198287 A1 | 8/2009 | Chiu |
| 2009/0254090 A1 | 10/2009 | Lizee |
| 2009/0264937 A1 | 10/2009 | Parrott |
| 2010/0036430 A1 | 2/2010 | Hartdegen et al. |
| 2010/0063506 A1 | 3/2010 | Fox et al. |
| 2010/0087822 A1 | 4/2010 | Groiso |
| 2010/0131014 A1 | 5/2010 | Peyrot et al. |
| 2010/0211115 A1 | 8/2010 | Tyber et al. |
| 2010/0237128 A1 | 9/2010 | Miller et al. |
| 2011/0008643 A1 | 1/2011 | Shaw et al. |
| 2011/0060372 A1 | 3/2011 | Allison |
| 2011/0144703 A1 | 6/2011 | Krause et al. |
| 2011/0224725 A1 | 9/2011 | De Canniere et al. |
| 2011/0247731 A1 | 10/2011 | Gordon |
| 2011/0313473 A1 | 12/2011 | Prandi et al. |
| 2012/0116465 A1 | 5/2012 | Elahinia et al. |
| 2013/0030437 A1 | 1/2013 | Fox |
| 2013/0066435 A1 | 3/2013 | Averous et al. |
| 2013/0123785 A1 | 5/2013 | Fonte |
| 2013/0206815 A1 | 8/2013 | Fox |
| 2013/0231667 A1 | 9/2013 | Taylor et al. |
| 2013/0300437 A1 | 11/2013 | Grosjean et al. |
| 2014/0014553 A1 | 1/2014 | Knight et al. |
| 2014/0018809 A1 | 1/2014 | Allen |
| 2014/0020333 A1 | 1/2014 | Knight et al. |
| 2014/0024002 A1 | 1/2014 | Knight et al. |
| 2014/0097228 A1 | 4/2014 | Taylor et al. |
| 2014/0257420 A1 | 9/2014 | Fox |
| 2014/0277516 A1 | 9/2014 | Miller et al. |
| 2014/0324048 A1 | 10/2014 | Fox |
| 2014/0358187 A1 | 12/2014 | Taber et al. |
| 2014/0358247 A1 | 12/2014 | Fox et al. |
| 2015/0238237 A1 | 8/2015 | Madjarov |
| 2015/0238238 A1 | 8/2015 | Cheney |
| 2016/0051284 A1 | 2/2016 | Cronen |
| 2016/0089190 A1 | 3/2016 | Taber |
| 2016/0095638 A1 | 4/2016 | Reimels |
| 2016/0135808 A1 | 5/2016 | Anderson |
| 2016/0199060 A1 | 7/2016 | Morgan et al. |
| 2016/0235460 A1 | 8/2016 | Wahl |
| 2017/0000482 A1 | 1/2017 | Averous et al. |
| 2017/0231625 A1 | 8/2017 | Handie |

FOREIGN PATENT DOCUMENTS

| | | |
|---|---|---|
| FR | 2874166 A1 | 2/2006 |
| FR | 2901119 A1 | 11/2007 |
| IL | 64726 A | 2/1985 |

(56) References Cited

FOREIGN PATENT DOCUMENTS

| WO | 2009/091770 A1 | 7/2009 |
|---|---|---|
| WO | 2014087111 A1 | 6/2014 |

OTHER PUBLICATIONS

Gruszka et al., The Durability of the Intrascaphoid Compression of Headless Compression Screws: In Vitro Study, JHS, vol. 37A, Jun. 2012, 1142-1150.
S. Cai et al., Texture evolution during nitinol martensite detwinning and phase transformation, Appl. Phys. Lett. 103, 2013, 241909.
Supplementary European Search Report for EP Application 14861059.5 dated Sep. 6, 2017.
International Preliminary Report on Patentability for PCT Application No. PCT/US2014/065406 dated May 17, 2016.
International Preliminary Report on Patentability for PCT Application No. PCT/US2014/065553 dated May 17, 2016.
International Preliminary Report on Patentability for PCT Application No. PCT/US2015/020598 dated Sep. 13, 2016.
International Preliminary Report on Patentability for PCT Application No. PCT/US2015/028328 dated Nov. 1, 2016.
International Preliminary Report on Patentability for PCT Application No. PCT/US2016/015432 dated Aug. 10, 2017.
International Preliminary Report and Written Opinion for PCT Application No. PCT/US2014/065406 dated Feb. 24, 2015.
International Preliminary Report and Written Opinion for PCT Application No. PCT/US2014/065553 dated Feb. 24, 2015.
International Preliminary Report and Written Opinion for PCT Application No. PCT/US2015/020598 dated Jun. 12, 2015.
International Preliminary Report and Written Opinion for PCT Application No. PCT/US2015/028328 dated Aug. 4, 2015.
International Preliminary Report and Written Opinion for PCT Application No. PCT/US2016/015432 dated Apr. 21, 2016.
International Preliminary Report and Written Opinion for PCT Application No. PCT/US2016/023980 dated Jul. 21, 2016.
Non-Final Office Action for U.S. Appl. No. 14/540,351 dated Apr. 19, 2017.
U.S. Appl. No. 15/651,530 filed Jul. 7, 2017, entitled "Staples for Generating and Applying Compression within a Body".
Non-Final Office Action for U.S. Appl. No. 15/650,210 dated Oct. 4, 2017.
Non-Final Office Action for U.S. Appl. No. 15/684,183 dated Oct. 10, 2017.
Restriction Requirement for U.S. Appl. No. 14/699,837 dated Sep. 13, 2017.
U.S. Appl. No. 14/540,351 filed Nov. 13, 2014, entitled "Staples for Generating and Applying Compression within a Body".
Supplementary European Search Report for EP Application 14862438.0 dated Jun. 12, 2017.
Supplementary European Search Report for EP Application No. 14861238.5 dated Jun. 12, 2017.
U.S. Appl. No. 14/699,837 filed Apr. 29, 2015, entitled "Controlling the Unloading Stress of Nitinol Devices and/or Other Shape Memory Material Devices".
U.S. Appl. No. 15/079,770 filed Mar. 24, 2016, entitled "Staples for Generating and Applying Compression within a Body".
U.S. Appl. No. 15/684,183 filed Aug. 23, 2017, entitled "Staples for Generating and Applying Compression within a Body".
U.S. Appl. No. 15/650,210, filed Jul. 14, 2017, entitled "Staples for Generating and Applying Compression within a Body".

\* cited by examiner

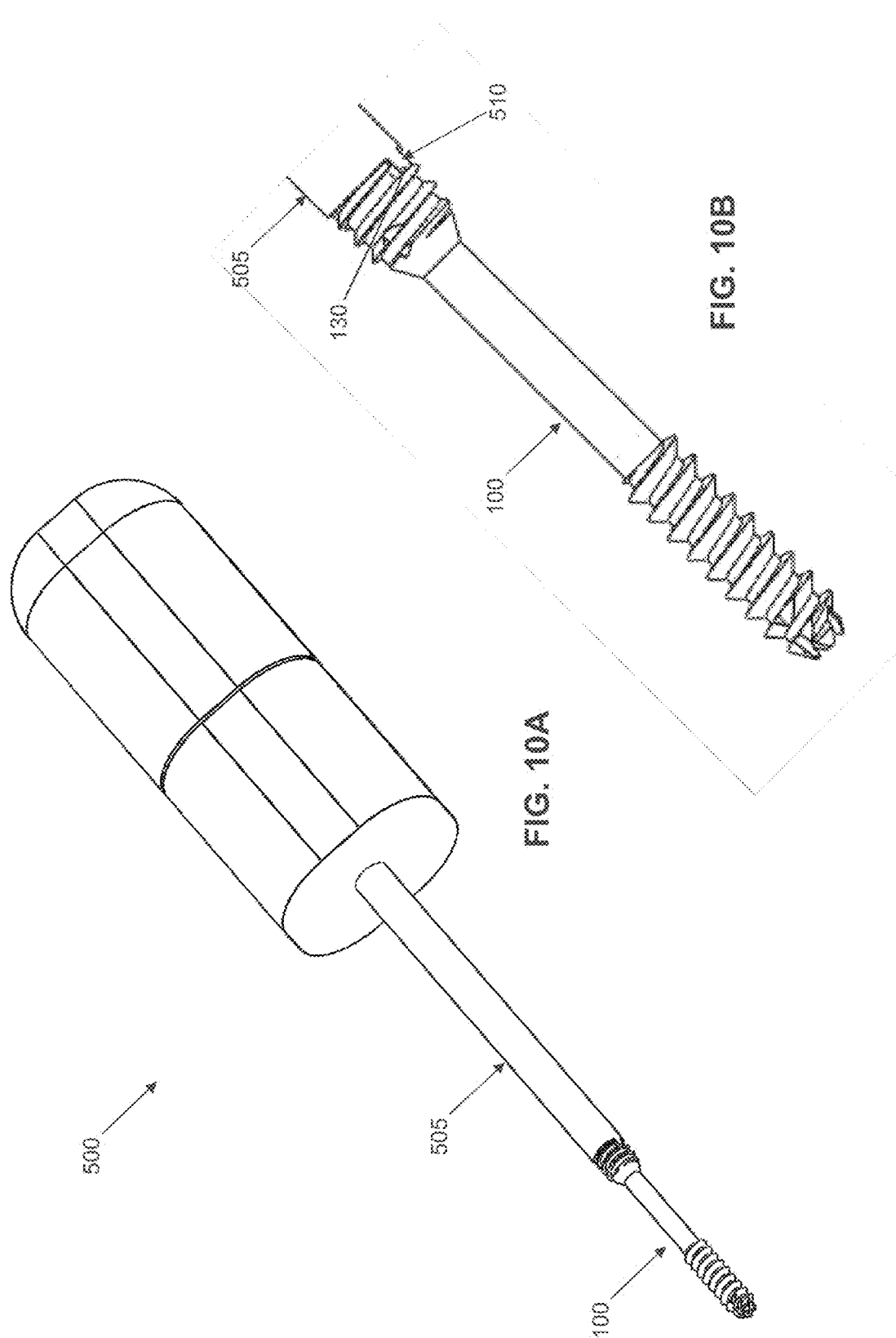

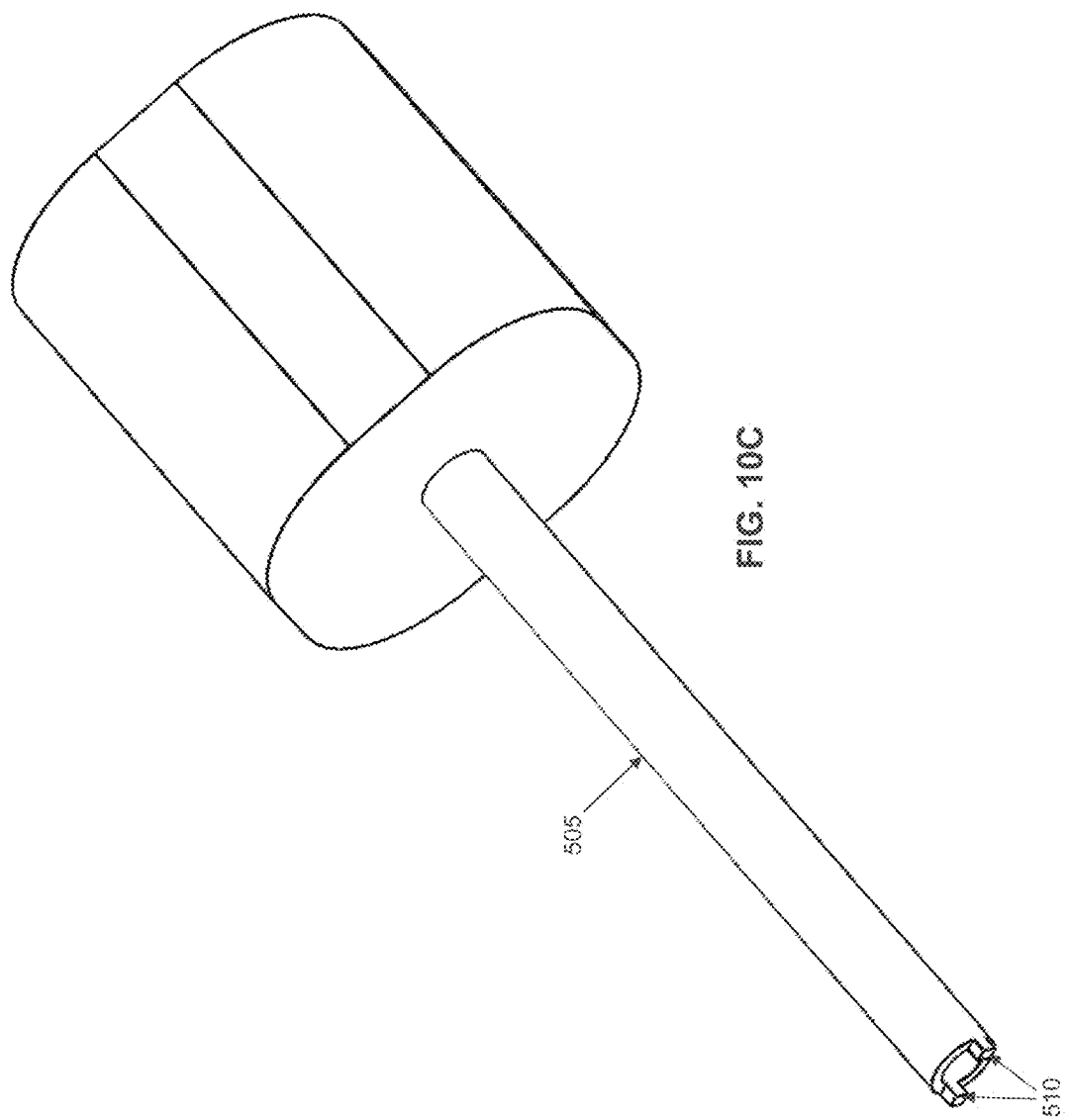

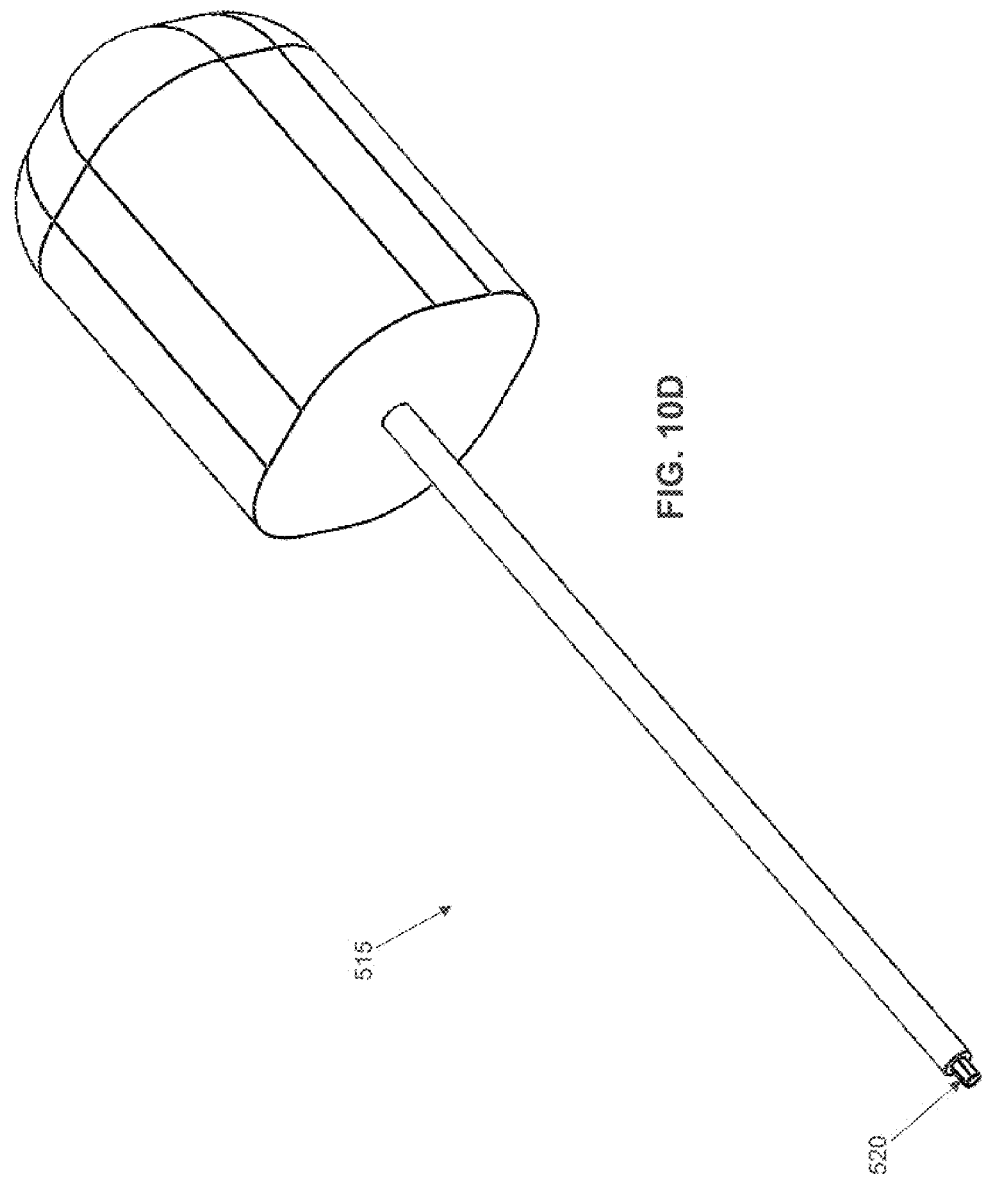

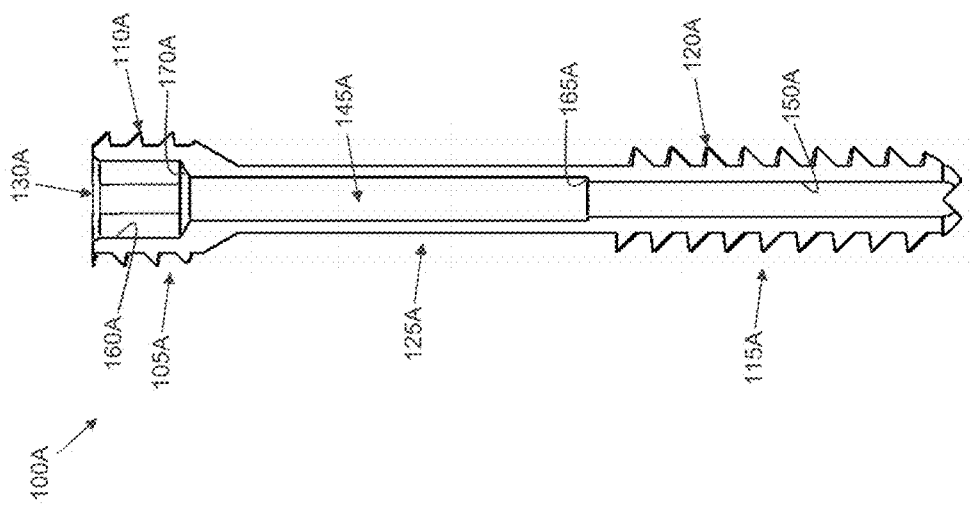

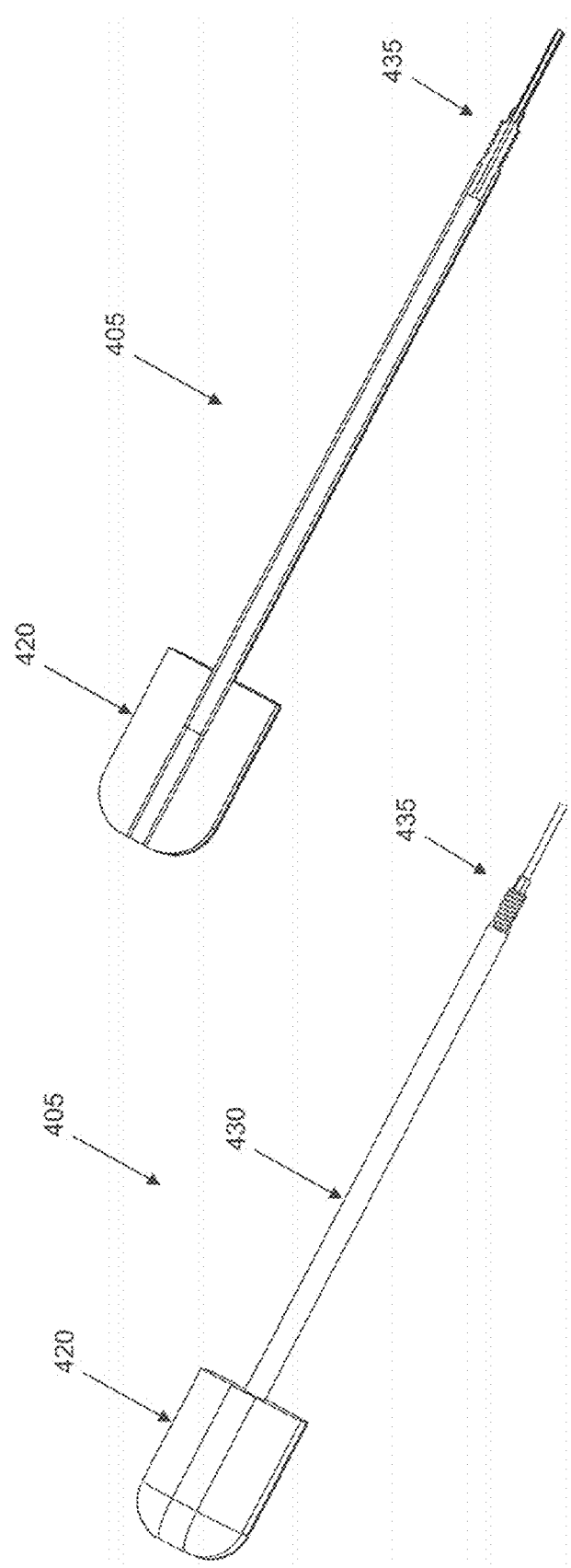

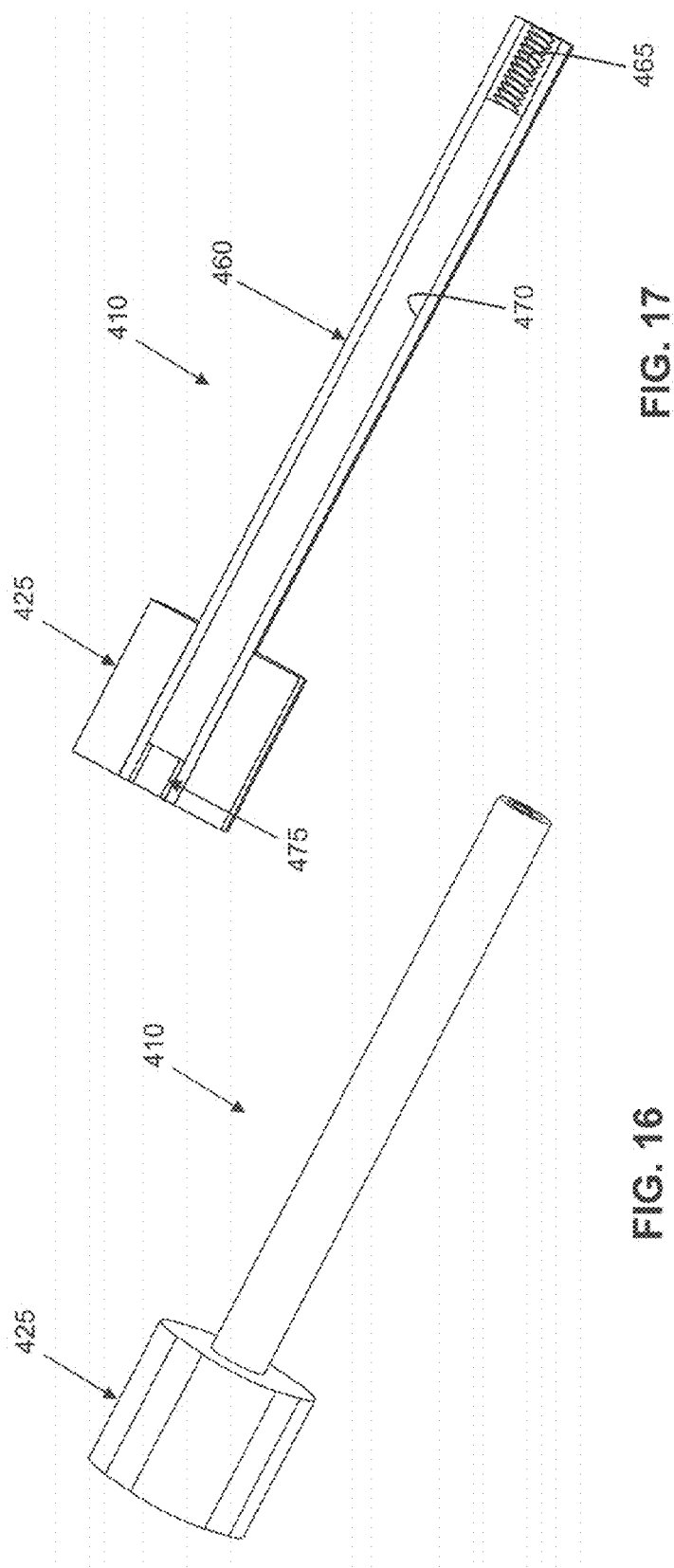

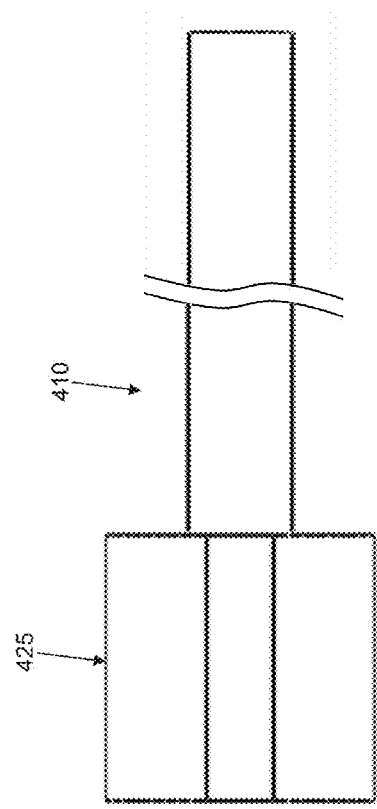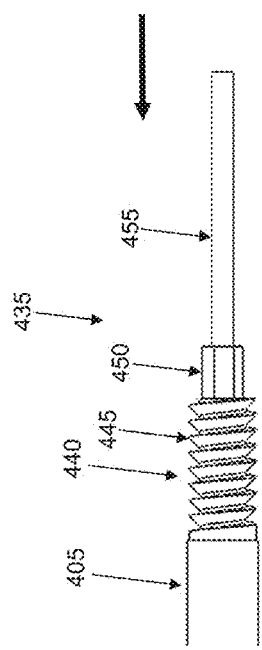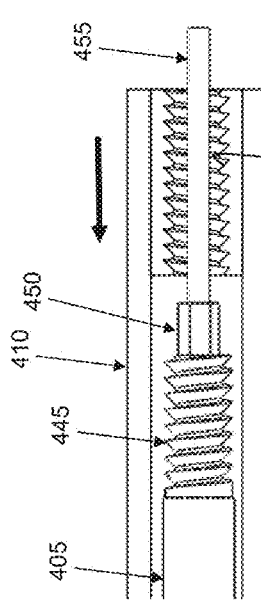

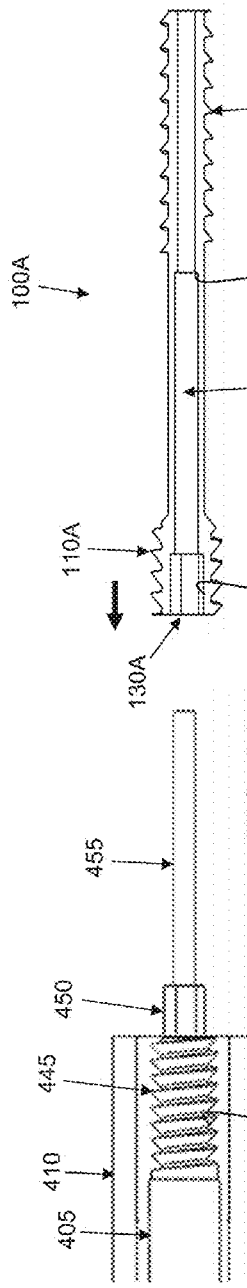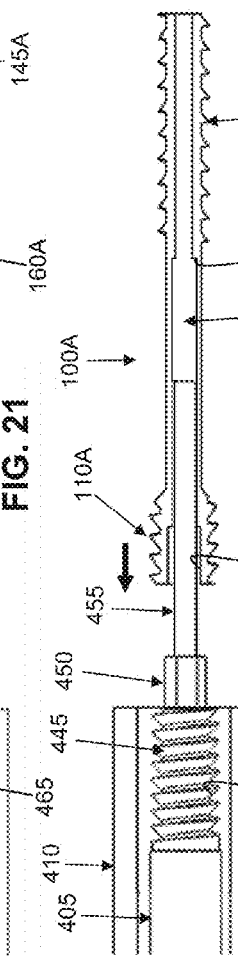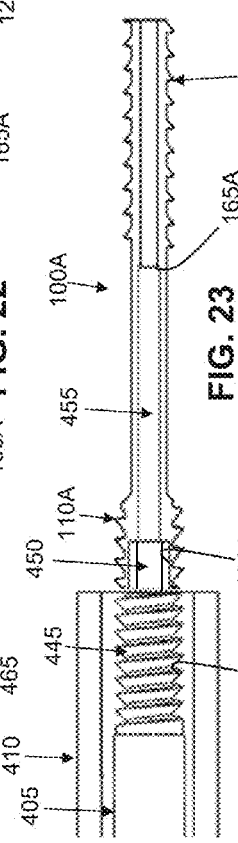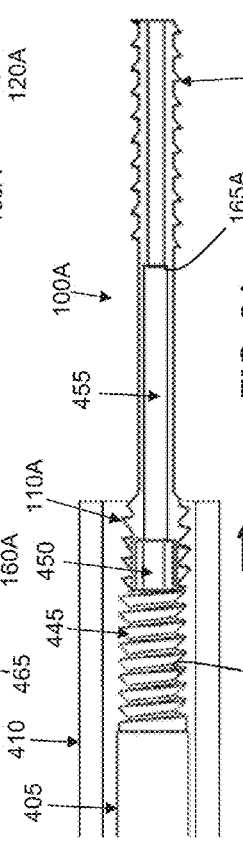

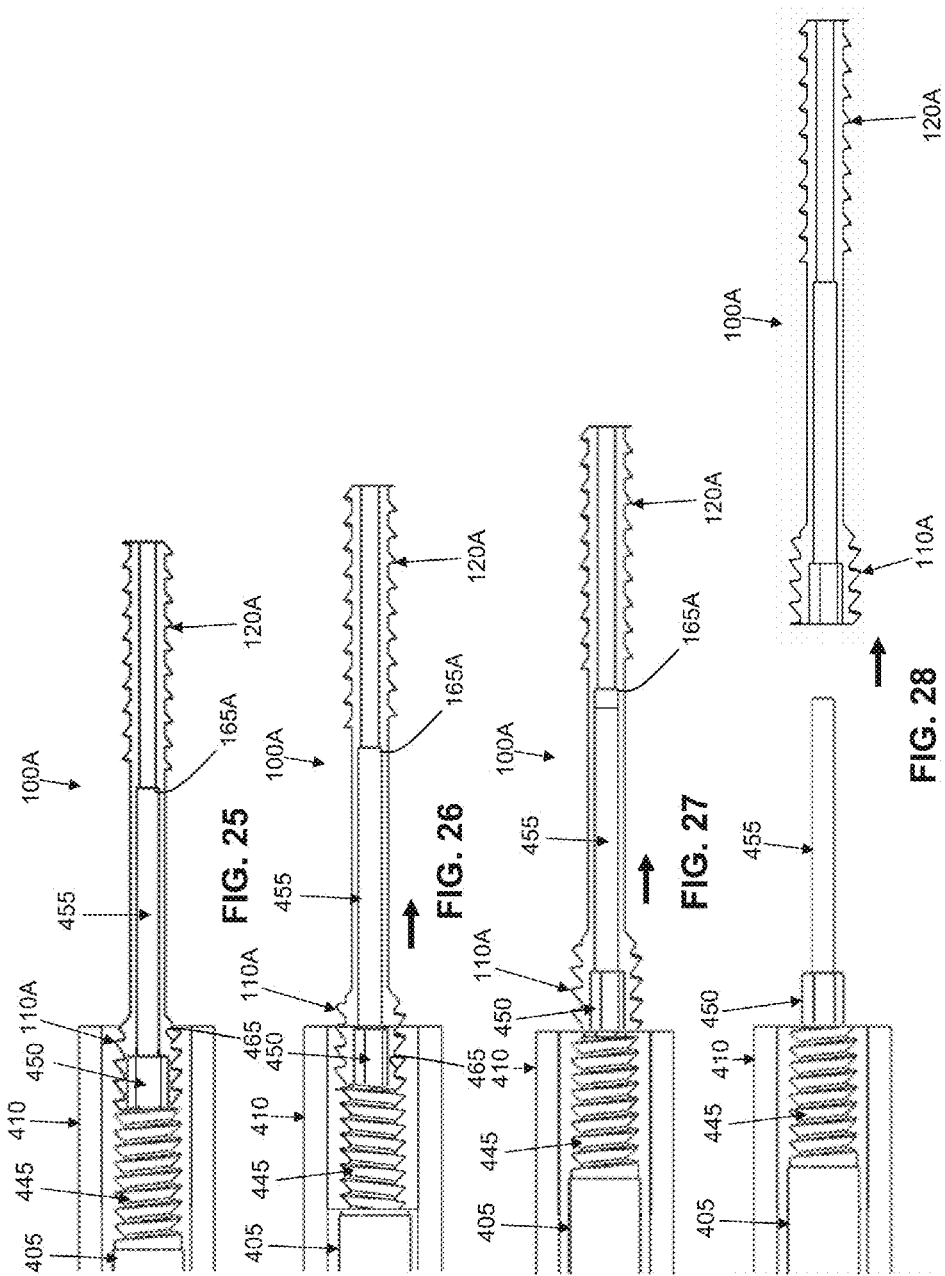

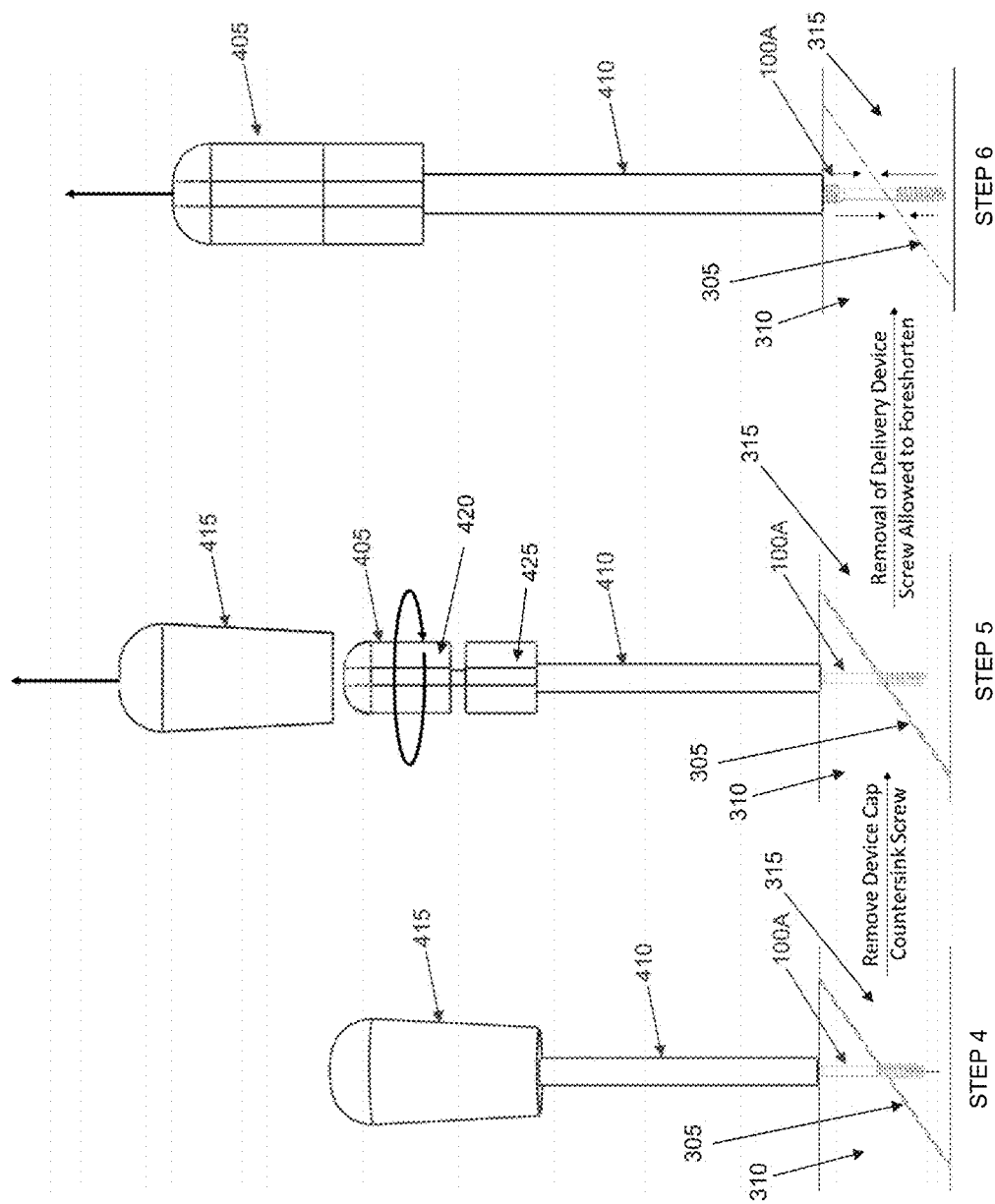

US 9,861,413 B2

SCREWS FOR GENERATING AND APPLYING COMPRESSION WITHIN A BODY

REFERENCE TO PENDING PRIOR PATENT APPLICATIONS

This patent application:

(1) claims benefit of prior U.S. Provisional Patent Application Ser. No. 61/902,338, filed Nov. 11, 2013 by MX Orthopedics, Corp. and Matthew Palmer et al. for SUPERELASTIC AND SHAPE MEMORY CANNULATED INTERFRAGMENTARY BONE COMPRESSION SCREW; and (2) claims benefit of prior U.S. Provisional Patent Application Ser. No. 61/903,820, filed Nov. 13, 2013 by MX Orthopedics, Corp. and Matthew Palmer et al. for BONE STAPLES, INTRAMEDULLARY FIXATION DEVICES, SOFT TISSUE ANCHORS AND PINS SCREWS CAN BE SHORTENED IN VIVO TO IMPROVE FRACTURE REDUCTION BY USING SUPERELASTIC OR SHAPE MEMORY EFFECT CHARACTERISTICS OF NITINOL.

The two (2) above-identified patent applications are hereby incorporated herein by reference.

FIELD OF THE INVENTION

The present invention relates to screws for generating and applying compression to a site in a human or animal body in order to effect healing of diseased or damaged tissue. The invention finds particular utility in the field of orthopedics and specifically for reducing fractures and generating and maintaining compression between bone fragments. While the invention has application throughout the body, its utility will be illustrated herein in the context of the repair of injured bone tissue, such as the scaphoid of the wrist, diaphysis of the fifth metatarsal, and the proximal interphalangeal joint of the second, third, fourth, or fifth toe.

BACKGROUND OF THE INVENTION

In the field of orthopedic surgery, it is common to rejoin broken bones. The success of the surgical procedure often depends on the successful approximation of the bone and on the amount of compression achieved between the bone fragments. If the surgeon is unable to bring the bone fragments into close contact, a gap will exist between the bone fragments and the bone tissue will need to fill that gap before complete healing can take place. Furthermore, gaps between bone fragments that are too large allow motion to occur between the bone fragments, disrupting the healing tissue and thus slowing the healing process. Optimal healing requires that bone fragments be in close contact with each other, and for a compressive load to be applied and maintained between the fragments. Compressive strain between bone fragments has been found to accelerate the healing process in accordance with Wolf's Law.

Broken bones can be rejoined using screws, staples, plates, pins, intramedullary devices, and other devices known in the art. These devices are designed to assist the surgeon with reducing the fracture and creating a compressive load between the bone fragments. Screws are typically manufactured from either titanium or stainless steel alloys and may be lag-type or headless. Lag screws have a distal threaded region and an enlarged head. The head contacts the cortical bone surface and the action of the threaded region reduces the fracture and generates a compressive load. Headless screws typically have a threaded proximal region and a threaded distal region. A differential in thread pitch between the two regions generates compression across the fracture site. There also exists fully threaded headless compression screws that have a thread pitch differential over the length of the single continuous thread.

While these devices are designed to bring the bone fragments into close contact and to generate a compressive load between the bone fragments, these devices do not always succeed in accomplishing this objective. Among other things, the differential pitch on headless bone screws is able to reduce gaps and to initially create compressive loads; however, it is widely reported that the compressive load dissipates rapidly as the bone relaxes and remodels around the threads. Furthermore, with headless bone screws comprising two separated threads, the gap reduction is limited by relatively small pitch differential and short thread length.

Thus there exists a clinical need for fixation devices that are able to bring bone fragments into close proximity with each other, generate a compressive load, and maintain that compressive load for a prolonged period of time while healing occurs.

SUMMARY OF THE INVENTION

The present invention provides a novel fixation device which is able to bring bone fragments into close proximity with each other, generate a compressive load, and maintain that compressive load for a prolonged period of time while healing occurs.

Among other things, the present invention comprises the provision and use of a compression screw manufactured from a shape memory material (e.g., a material capable of exhibiting superelasticity and/or a temperature-induced shape change). The shape memory material may be a metal alloy (e.g., Nitinol) or a polymer (e.g., appropriately processed PEEK). The compression screw is designed to engage bone fragments and to generate compression between the bone fragments. The compression screw has a proximal threaded region and a distal threaded region. The thread pitch on the proximal threaded region is finer than the thread pitch on the distal threaded region (i.e., the thread pitch on the proximal threaded region has more threads per inch than the thread pitch on the distal threaded region). This pitch differential aids in reducing fractures and in generating compression between the bone fragments. The thread geometry on the proximal threaded region and the distal threaded region are mirrored to create a "book-end" effect that increases the compression holding capabilities of the screw (e.g., the thread geometry on the proximal threaded region has an incline in the proximal direction and a flat surface in the distal direction that is substantially perpendicular to the longitudinal axis of the screw; the thread geometry on the distal threaded region is mirrored, having an incline in the distal direction and a flat surface in the proximal direction that is substantially perpendicular to the longitudinal axis of the screw). The two threaded regions are connected by a hollow central bridge region. The hollow central bridge region can be strained and reversibly elongated, e.g., up to about 8% where the compression screw is formed from Nitinol. The hollow central bridge region may be strained and reversibly elongated prior to implantation; by releasing that strain after implantation of the compression screw across the fracture line, the contracting hollow central bridge region can aid in fracture reduction and provide additional therapeutic compression to the bone fracture, whereby to provide superior healing.

In one preferred form of the invention, there is provided a compression screw system, said compression screw system comprising:

a compression screw comprising a shaft, a screw thread formed on said shaft at a distal location, and a bone-engaging feature formed on said shaft at a proximal location, wherein at least a portion of said shaft disposed between said screw thread and said bone-engaging feature is capable of being stretched; and a holding element connectable to said compression screw for releasably holding said at least a portion of said shaft in a stretched condition.

In another preferred form of the invention, there is provided a method for treating a fracture, said method comprising:

providing a compression screw;

longitudinally stretching said compression screw so that said compression screw is in a longitudinally stretched condition;

holding said compression screw in its longitudinally stretched condition;

inserting said compression screw into bone while said compression screw is in its longitudinally stretched condition so that said compression screw extends across the fracture; and releasing said compression screw from its longitudinally stretched condition so as to apply compression across the fracture.

In another preferred form of the invention, there is provided a compression screw system, said compression screw system comprising:

a compression screw comprising a shaft capable of being stretched, said shaft having a proximal end, a distal end and a lumen extending therebetween, said proximal end of said shaft comprising a proximal screw thread and said distal end of said shaft comprising a distal screw thread, said lumen comprising a distal bore, an intermediate counterbore communicating with said distal bore so as to define a first shoulder, and a proximal counterbore communicating with said intermediate counterbore so as to define a second shoulder, said proximal counterbore comprising a connection feature and said proximal end of said shaft comprising a drive feature for turning said compression screw; and an internal retaining pin comprising a pin shaft having a proximal end, a distal end and a lumen extending therebetween, said proximal end of said pin shaft comprising a second connection feature configured to mate with said connection feature of said proximal counterbore of said compression screw, and said distal end of said pin shaft terminating in a distal end surface, said internal retaining pin comprising a pin drive feature for turning said internal retaining pin, and said internal retaining pin being sized such that, when said shaft of said compression screw is stretched, and when said internal retaining pin is inserted into said lumen of said compression screw such that said second connection feature of said internal retaining pin is engaged with said connection feature of said proximal counterbore of said compression screw and contacts said second shoulder of said compression screw, said distal end surface of said pin shaft engages said first shoulder of said compression screw, whereby to prevent foreshortening of the stretched compression screw.

In another preferred form of the invention, there is provided a compression screw system, said compression screw system comprising:

a compression screw comprising a shaft capable of being stretched, said shaft having a proximal end, a distal end and a lumen extending therebetween, said proximal end of said shaft comprising a proximal screw thread and said distal end of said shaft comprising a distal screw thread, said lumen comprising a distal bore, an intermediate counterbore communicating with said distal bore so as to define a first shoulder, and a proximal counterbore communicating with said intermediate counterbore so as to define a second shoulder, said proximal counterbore comprising a drive feature for turning said compression screw;

a cannulated inner driver comprising a shaft having a proximal end, a distal end, and a lumen extending therebetween, said distal end of said shaft comprising a compression screw interface comprising an interface shaft having a proximal end and a distal end, said proximal end of said interface shaft comprising a proximal screw thread matching said proximal screw thread of said compression screw, said distal end of said interface shaft terminating in a distal end surface, and said compression screw interface comprising an interface drive feature for engaging said drive feature of said compression screw, whereby to allow said cannulated inner driver to turn said compression screw;

a cannulated outer driver comprising a shaft having a proximal end, a distal end, and a lumen extending therebetween, said distal end of said shaft of said cannulated outer driver comprising an internal screw thread sized to mate with said proximal screw thread of said compression screw interface of said cannulated inner driver and said proximal screw thread of said compression screw; and a coupling cap for selectively coupling said cannulated outer driver to said cannulated inner driver;

said compression screw interface of said cannulated inner driver being sized such that, when said shaft of said compression screw is stretched, and when said compression screw is mounted on said compression screw interface such that said interface shaft is inserted into said lumen of said compression screw such that said proximal screw thread of said compression screw is disposed adjacent to said proximal screw thread of said compression screw interface, said interface drive feature of said compression screw interface engages said drive feature of said compression screw and said distal end surface of said interface shaft engages said first shoulder of said compression screw, whereby to prevent foreshortening of said stretched compression screw.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 10A-10E are schematic views showing a two-part driver which may be used to deploy the compression screw system shown in FIG. 1;

FIG. 12 is a schematic view showing the compression screw of the compression screw system shown in FIG. 11;

FIGS. 13-15 are schematic views showing the cannulated inner driver of the compression screw system shown in FIG. 11;

FIGS. 16 and 17 are schematic views showing the cannulated outer driver of the compression screw system shown in FIG. 11;

FIGS. 18-24 are schematic views showing how the already-strained compression screw (i.e., the already-stretched compression screw) may be retained in that strained (i.e., stretched) condition by mounting the strained (i.e., stretched) compression screw on the cannulated inner driver and then securing the strained (i.e., stretched) compression screw on the cannulated inner driver by means of the cannulated outer driver;

FIGS. 25-28 are schematic views showing how the strained (i.e., stretched) compression screw may be deployed from the cannulated outer driver and the cannulated inner driver causing the screw to release from the driver system and foreshorten; and FIGS. 29 and 30 are schematic views showing how the compression screw system of FIG. 11 may be used to treat a fracture.

DETAILED DESCRIPTION OF THE PREFERRED EMBODIMENTS

Figure 1:
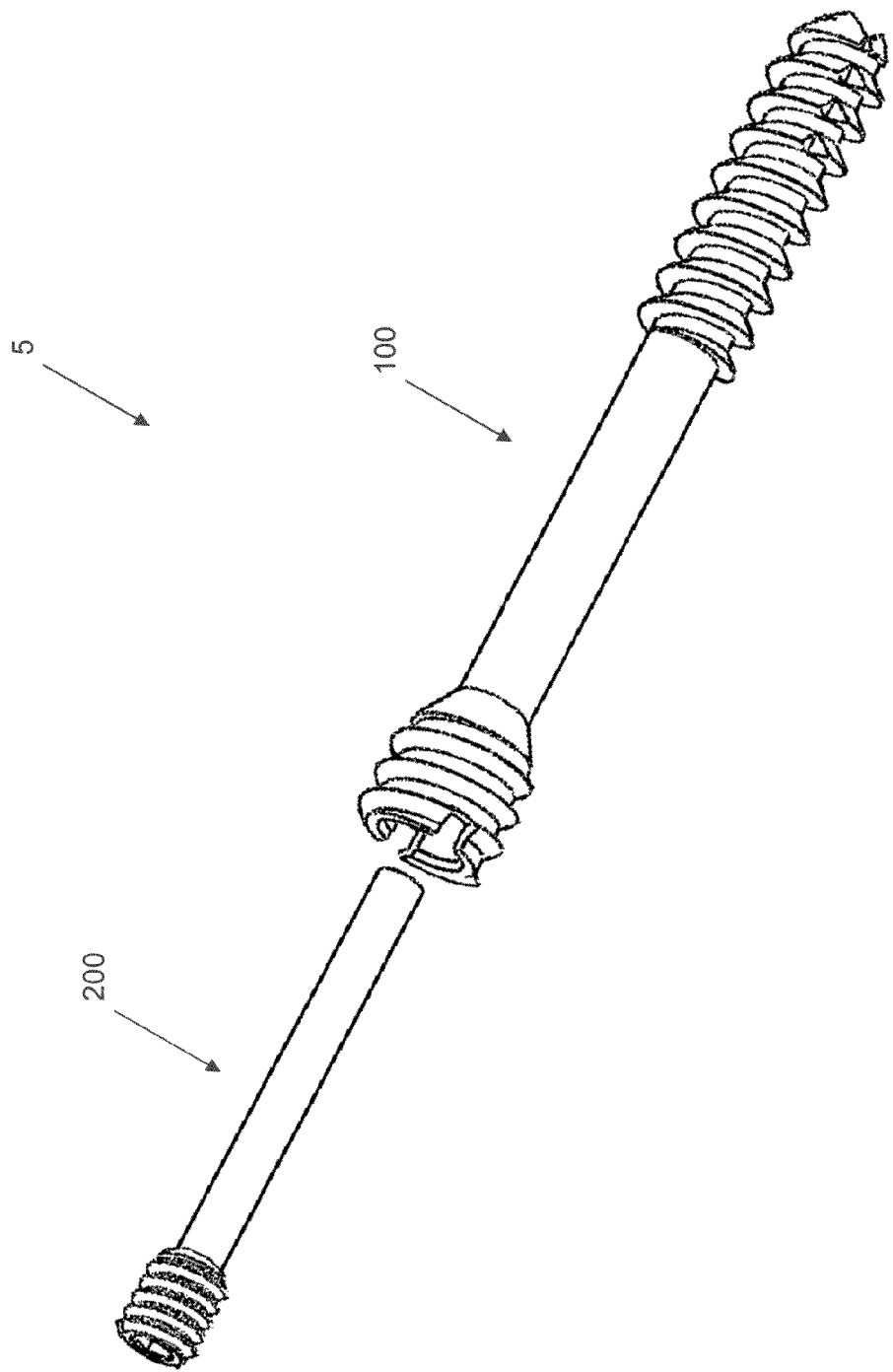
FIG. 1 is a schematic view showing a novel compression screw system formed in accordance with the present invention.

Looking first at FIG. 1, there is shown a novel compression screw system 5 for bringing bone fragments into close proximity with each other, generating a compressive load, and maintaining that compressive load for a prolonged period of time while the bone tissue heals. Novel compression screw system 5 generally comprises a compression screw 100 and an internal retaining pin 200, as will hereinafter be discussed.

In one preferred form of the invention, compression screw 100 and internal retaining pin 200 are provided in the form of a sterilized kit. The kit may include additional instruments to aid in the implantation of the screw (e.g., k-wire, drill bit, screw size guide, etc.).

Figure 3:
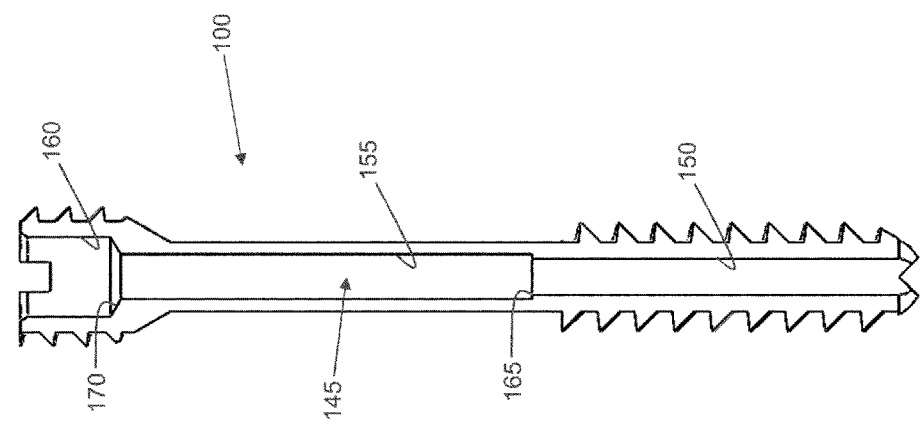
FIGS. 2 and 3 are schematic views showing the compression screw of the compression screw system shown in FIG. 1.
Figure 2:
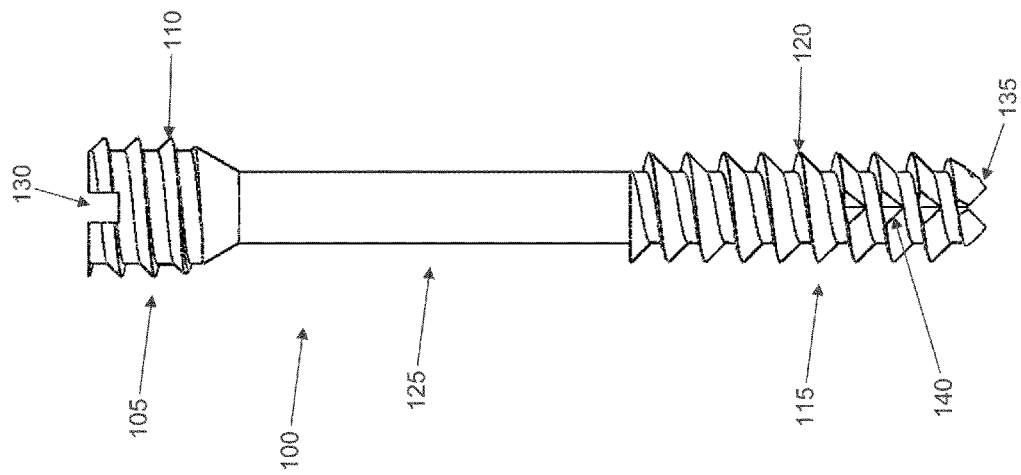

Compression screw 100 is shown in greater detail in FIGS. 2 and 3. Compression screw 100 is manufactured from a shape memory material (e.g., a material capable of exhibiting superelasticity and/or a temperature-induced shape change). The shape memory material may be a metal alloy (e.g., Nitinol) or a polymer (e.g., appropriately processed PEEK). Compression screw 100 is designed to engage bone fragments and generate compression between the bone fragments. Compression screw 100 comprises a proximal threaded region 105 comprising proximal screw thread 110 and a distal threaded region 115 comprising distal screw thread 120. The thread pitch of proximal screw thread 110 is finer than the thread pitch of distal screw thread 120 (i.e., the thread pitch on proximal threaded region 105 has more threads per inch than the thread pitch on distal threaded region 115). This pitch differential aids in reducing fractures and generating compression. The respective thread geometry on proximal threaded region 105 and distal threaded region 115 are mirrored, creating a "book-end" effect that increases the compression holding capabilities of compression screw 100 when compression screw 100 extends across a fracture line in bone (e.g., the thread geometry on proximal threaded region 105 has an incline in the proximal direction and a flat surface in the distal direction that is substantially perpendicular to the longitudinal axis of the screw; the thread geometry on distal threaded region 105 is mirrored, having an incline in the distal direction and a flat surface in the proximal direction that is substantially perpendicular to the longitudinal axis of the screw).

Proximal threaded region 105 and distal threaded region 115 are connected by a hollow central bridge region 125. Hollow central bridge region 125 can be strained and reversibly elongated by virtue of the fact that compression screw 100 is manufactured from a shape memory material (e.g., a material capable of exhibiting superelasticity and/or a temperature-induced shape change), which may be a metal alloy (e.g., Nitinol) or a polymer (e.g., appropriately processed PEEK). By way of example but not limitation, where compression screw 100 is formed out of Nitinol, hollow central bridge region 125 can be strained and reversibly elongated by up to 8% without taking a set. By straining and reversibly elongating hollow central bridge region 125 prior to implantation across a fracture line in bone, and by thereafter releasing that strain after implantation across the fracture line, contracting hollow central bridge region 125 can provide additional compression to the bone fracture.

Compression screw 100 comprises a drive feature 130 (e.g., a slot) in proximal threaded region 105 for engagement by an appropriate driver (not shown) of the sort well known in the art, whereby to turn compression screw 100 (e.g., into bone). Additionally, the distal threaded region 115 of compression screw 100 preferably comprises self-drilling features 135 (e.g., cutting edges) of the sort well known in the screw art, and self-tapping features 140 (e.g., flutes) of the sort well known in the screw art.

Compression screw 100 comprises a central lumen 145 which extends the length of the compression screw. Central lumen 145 generally comprises a distal bore 150, an intermediate counterbore 155 and a proximal counterbore 160. Intermediate counterbore 155 has a diameter which is wider than the diameter of distal bore 150, and an annular shoulder 165 is formed at the intersection of distal bore 150 and intermediate counterbore 155. Annular shoulder 165 preferably lies in a plane perpendicular to the longitudinal axis of the compression screw. Proximal counterbore 160 has a diameter which is wider than the diameter of intermediate counterbore 155, and an annular shoulder 170 is formed at the intersection of intermediate counterbore 155 and proximal counterbore 160. Proximal counterbore 160 is threaded, e.g., with an internal thread 175 (for purposes of clarity, not shown in FIG. 3, but shown in FIG. 7).

Figure 5:
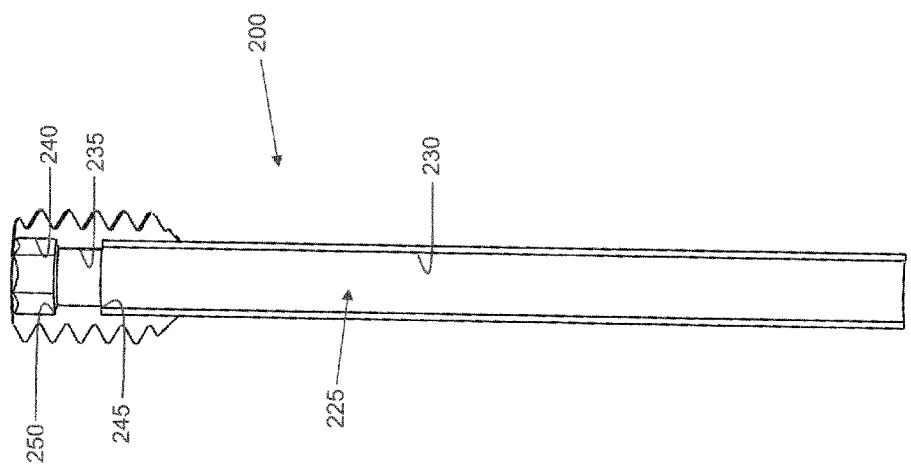
FIGS. 4 and 5 are schematic views showing the internal retaining pin of the compression screw system shown in FIG. 1.
Figure 4:
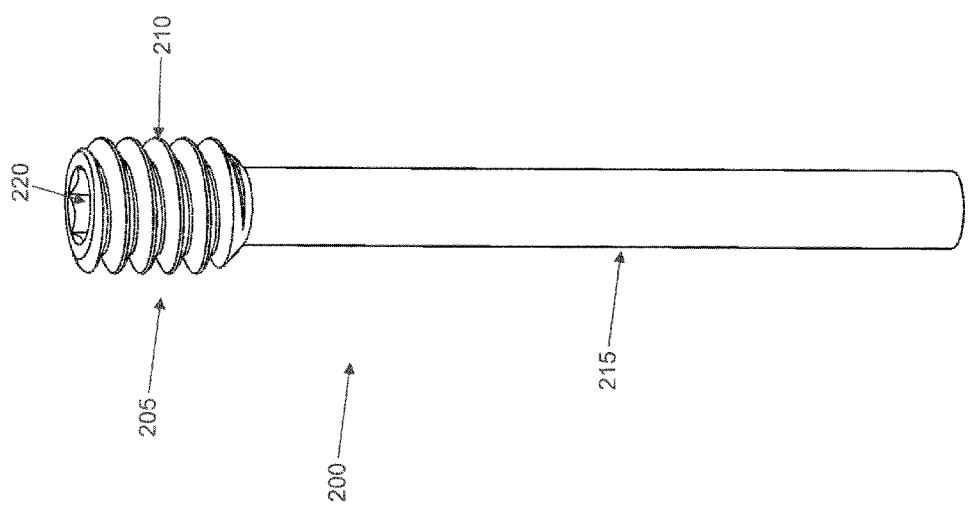

Internal retaining pin 200 is shown in greater detail in FIGS. 4 and 5. Internal retaining pin 200 comprises a proximal threaded region 205 comprising proximal screw thread 210 that engages internal thread 175 of proximal counterbore 160 of central lumen 145 of compression screw 100, as will hereinafter be discussed. Internal retaining pin 200 comprises a hollow distal cylindrical region 215 disposed distal to proximal threaded region 205. Hollow cylindrical region 215 is sized to be received in central lumen 145 of compression screw 100 and engage annular shoulder 165 of an already-strained (i.e., an already-stretched) compression screw 100, as will hereinafter be discussed in further detail.

More particularly, internal retaining pin 200 comprises proximal threaded region 205 and distal cylindrical region 215. Internal retaining pin 200 is cannulated so as to allow a k-wire to be passed through internal retaining pin 200 as will hereinafter be discussed, and has a drive feature 220 in its threaded proximal region 205 to facilitate turning internal retaining pin 200, whereby to insert internal retaining pin 200 into compression screw 100 or to remove internal retaining pin 200 from compression screw 100, as will hereinafter be discussed. To this end, internal retaining pin 200 comprises a central lumen 225 which extends the length of internal retaining pin 200. Central lumen 225 preferably comprises a distal section 230, an intermediate section 235 and a proximal section 240. Distal section 230 has a diameter which is wider than the diameter of intermediate section 235, and a shoulder 245 is formed at the intersection of distal section 230 and intermediate section 235. Proximal section 240 has a widest diameter which is wider than the diameter of intermediate section 235, and a shoulder 250 is formed at the intersection of intermediate section 235 and proximal section 240. Proximal section 240 has a hexagonal (or other non-circular) cross-section, whereby to provide the aforementioned drive feature 220, whereby to enable turning internal retaining pin 200 into, or out of, compression screw 100, as will hereinafter be discussed.

Figure 8:
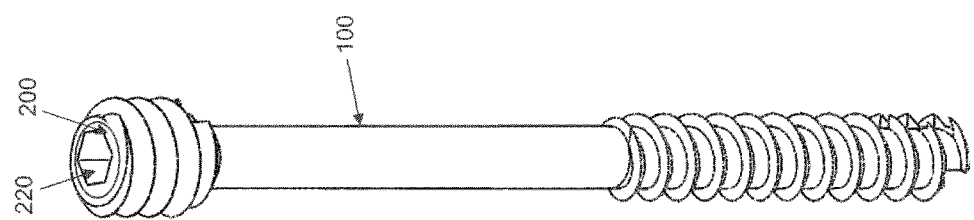
FIGS. 6-8 are schematic views showing the internal retaining pin disposed within the interior of a strained (i.e., stretched) compression screw.
Figure 7:
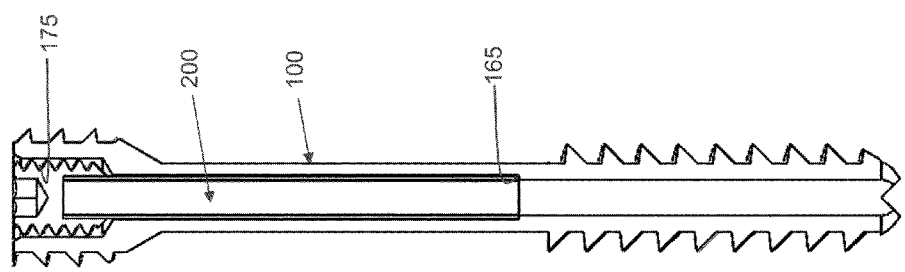
Figure 6:
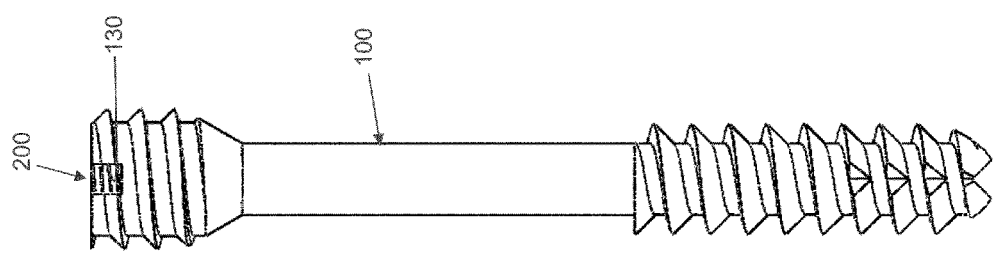

As seen in FIGS. 6-8, internal retaining pin 200 is configured to be selectively inserted into compression screw 100. More particularly, internal retaining pin 200 is configured to be selectively threaded into compression screw 100 so that distal cylindrical region 215 of internal retaining pin 200 is disposed in intermediate counterbore 155 of compression screw 100 when proximal threaded region 205 of internal retaining pin 200 is seated in proximal counterbore 160 of compression screw 100. As will hereinafter be discussed in further detail, internal retaining pin 200 is sized so that when compression screw 100 is strained (i.e., stretched) and proximal threaded region 205 of internal retaining pin 200 is fully seated in proximal counterbore 160 of compression screw 100, the distal end of distal cylindrical region 215 of internal retaining pin 200 abuts annular shoulder 165 of compression screw 100. See FIG. 7.

Internal retaining pin 200 is provided so as to selectively maintain compression screw 100 in a strained (i.e., stretched) configuration and, when internal retaining pin 200 is removed from compression screw 100, to allow compression screw 100 to attempt to return to its unstrained (i.e., unstretched) configuration.

Figure 9:
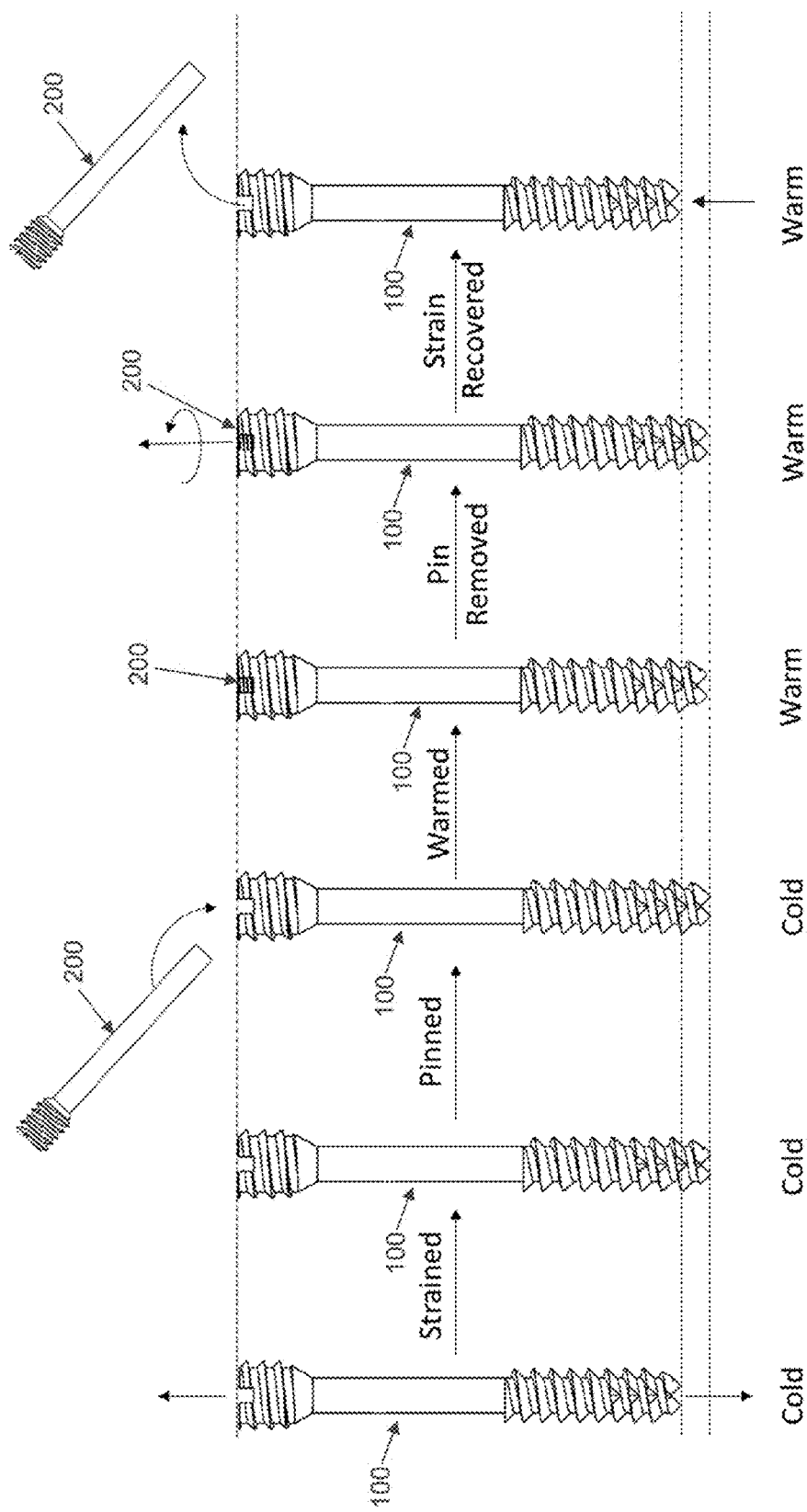
FIG. 9 is a schematic view showing how the compression screw may be strained (i.e., stretched), retained in that strained (i.e., stretched) condition by inserting the internal retaining pin within the interior of the strained (i.e., stretched) compression screw, and then allowed to foreshorten by removal of the internal retaining pin.

More particularly, and looking now at FIG. 9, with compression screw 100 maintained at a temperature below its austenite start temperature, more preferably below its martensite start temperature, and most preferably below is martensite finish temperature, compression screw 100 is gripped by its proximal threaded region 105 and its distal threaded region 115 and strained (i.e., stretched) using a stretching mechanism (not shown) of the sort which will be apparent to those skilled in the art in view of the present disclosure. As long as the temperature of compression screw 100 is maintained below the austenite start temperature, compression screw 100 will remain strained (i.e., stretched) even after the external strain load is removed.

Straining compression screw 100 in the "cold" condition is preferable because it takes considerably less force to strain the non-austenitic material. The load that is required to stretch the compression screw may be less than half that required to stress the material in its austenitic phase. Furthermore, the surface finish of the compression screw is critical to its biocompatibility. Prior to straining, the compression screw may be passivated to remove embedded surface contaminants that may have resulted from the manufacturing process. Passivation also creates a biocompatible oxide layer on the surface of the screw. Straining the compression screw with a high load (i.e., the type of high load required to stress the compression screw in an austenitic phase) can damage this biocompatible oxide layer, and can embed particles into the surface of the threaded regions of the compression screw. Lower loads (i.e., the type of loads required to stress the compression screw in a non-austenitic phase) will minimize any damage to the surface finish.

With compression screw 100 "cold" (i.e., maintained below its austenite start temperature, more preferably below its martensite start temperature, and most preferably below its martensite finish temperature) and strained (i.e., stretched), internal retaining pin 200 is installed in compression screw 100. More particularly, with compression screw 100 maintained below its austenite start temperature, internal retaining pin 200 is advanced into compression screw 100 so that proximal threaded region 205 of internal retaining pin 200 is fully seated in threaded proximal counterbore 160 of compression screw 100, and so that the distal end of internal retaining pin 200 abuts annular shoulder 165 in compression screw 100, whereby to lock compression screw 100 in its strained (i.e., stretched) state.

Compression screw 100 can now be warmed above its austenite start temperature and compression screw 100 will not foreshorten due to the presence of internal retaining pin 200 within compression screw 100.

However, when internal retaining pin 200 is thereafter removed from compression screw 100, compression screw 100 will attempt to revert back to its non-strained (i.e., unstretched) length, i.e., compression screw 100 will attempt to foreshorten. As a result, when a strained compression screw 100 is deployed across the fracture line in bone and internal retaining pin 200 is thereafter removed, the compressive force generated by the differential pitch of proximal threaded region 105 and distal threaded region 115 is supplemented by the additional compressive force created by the foreshortening of hollow central bridge region 125.

Note that compression screw 100 is configured so that the force that is generated as compression screw 100 foreshortens is less than the pullout force of distal threaded region 115 and proximal threaded region 105, so that compression screw 100 does not "tear through" the bone tissue when attempting to foreshorten. More particularly, compression screw 100 is specifically engineered so not to "tear through" the bone tissue. The compressive forces of compression screw 100 can be controlled by modulating the material properties of the compression screw and/or the geometry of the compression screw.

The percentage of cold work in the shape memory material forming compression screw 100 affects the compressive force generated by the compression screw. As the percentage of cold work increases, the compression force declines. A compression screw should, preferably, have between about 15% and 55% cold work to control the recovery force of the compression screw.

Another material property that affects the screw's compression force is the temperature differential between the body that the compression screw will be implanted into (assumed to be 37° C., which is the temperature of a human body) and the austenite finish temperature of the shape memory material forming compression screw 100. A smaller temperature differential between the two will result in the screw generating a small compressive load; conversely, the larger the temperature differential between the two will result in a screw generating a larger compressive load. The shape memory material that the compression screw is made out of should, preferably, have an austenite finish temperature of greater than about −10° C., resulting in a temperature differential of less than about 47° C. when the compression screw is implanted (assuming that the compression screw is implanted in a human body).

Screw geometry also affects the compression force generated. The cross-sectional area of the hollow central bridge region 125 affects the compression force. As the cross-sectional area increases, so does the compression force that the compression screw 100 will generate. In this respect it should be appreciated that it is beneficial for the compression force generated by foreshortening compression screw 100 to be constant as the bone relaxes and remodels. Thus, the cross-section of hollow central bridge region 125 of compression screw 100 preferably has a constant cross-section over its entire length. Cross-sections that are not uniform over the length of hollow central bridge region 125 can result in an increase or decrease in compression as the compression screw shortens.

The screws threads are critical for transmitting the compression force to the bone without "tearing through" the bone. The height of the screw threads, the number of threads per inch (pitch), and the geometry of the screw threads are all critical to the screw's ability to not "tear through" the bone. The proximal and distal threaded regions may be of different lengths. The length of the distal thread region may be equal to or greater than the length of the proximal thread region. The distal thread region should, preferably, be at least 20% of the total screw length. Additionally, the thread height of the distal threads should, preferably, be equal to or greater than the thread height of the proximal threads.

The distal thread geometry may also be mirrored from that of the proximal thread geometry. This creates threaded regions where the load-bearing thread face is nearly perpendicular to the longitudinal axis of the compression screw. The resulting thread form has high shear strength.

Figure 10:
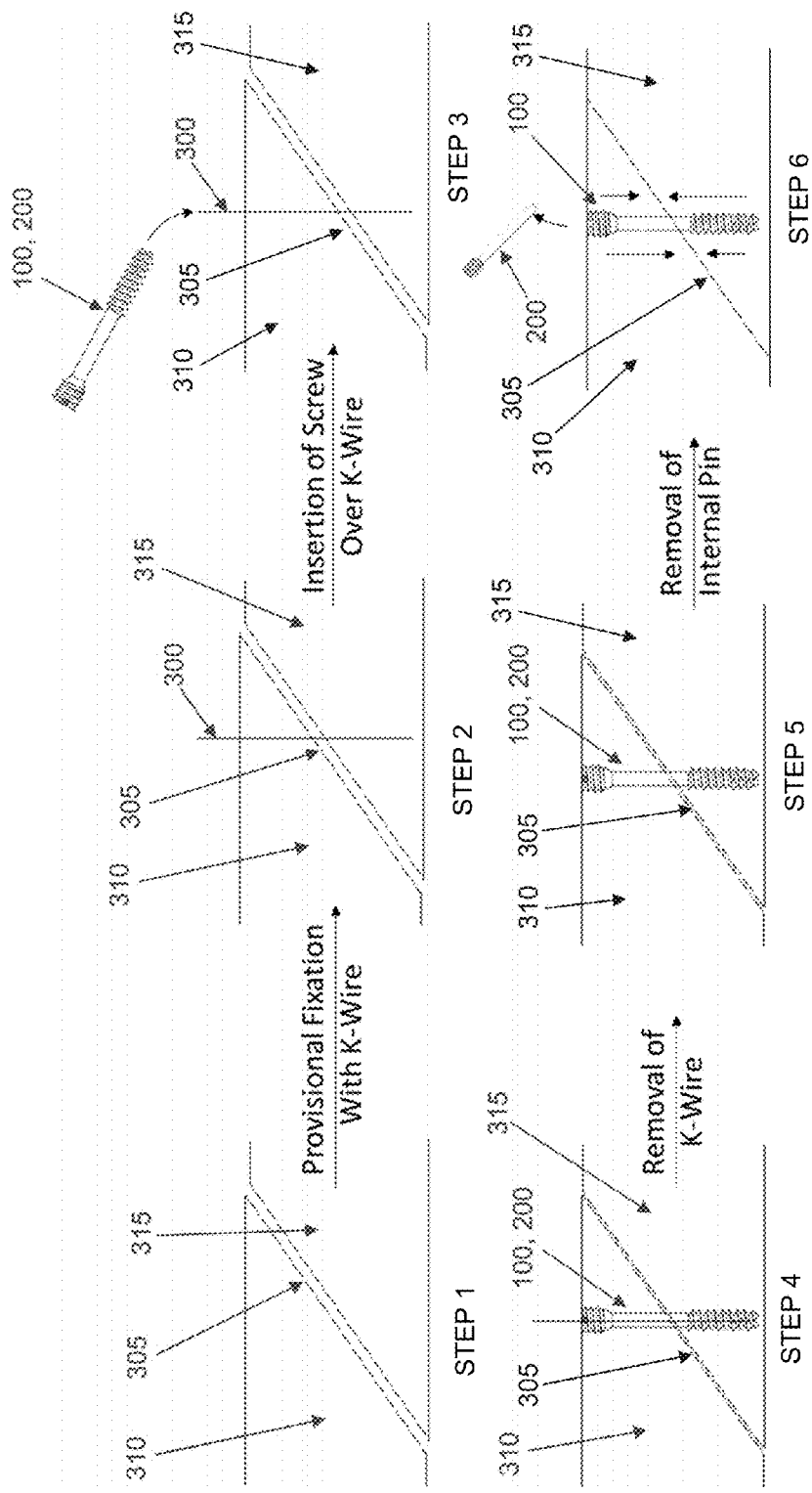
FIG. 10 is a schematic view showing how the compression screw system of FIG. 1 may be used to treat a fracture.
Figure 10E:
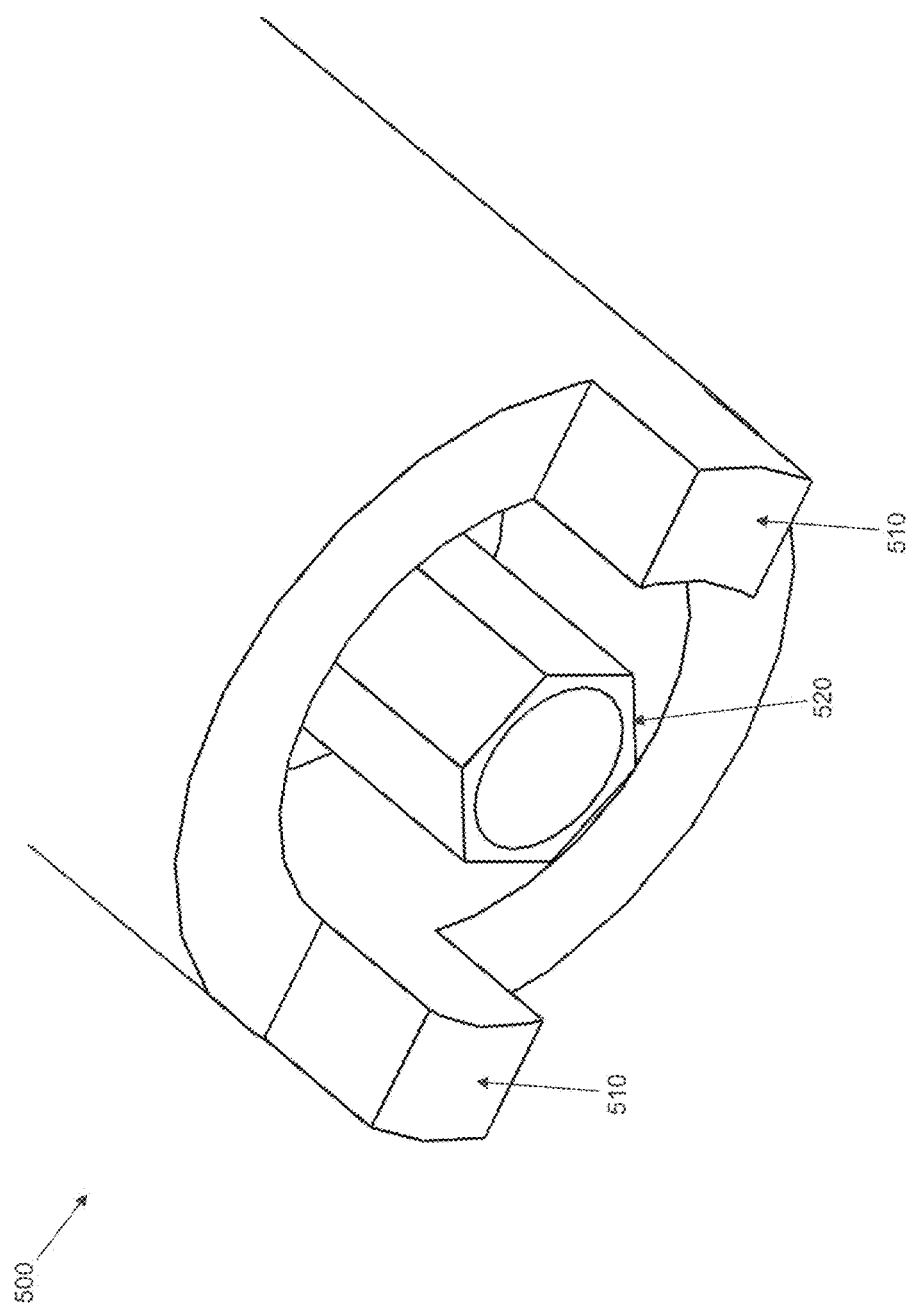

Looking now at FIG. 10, compression screw system 5 can be used to aid in the healing of fractured bone, e.g., the scaphoid of the wrist, diaphysis of the fifth metatarsal, and the proximal interphalangeal joint of the second, third, fourth or fifth toe. More particularly, in one preferred form of the invention, a k-wire 300 is inserted across a fracture line 305 to provisionally stabilize bone fragments 310, 315. A strained (i.e., stretched) compression screw 100, with internal retaining pin 200 disposed therein, is then slid over k-wire 300 and threaded into bone fragments 310, 315 so that compression screw 100 extends across fracture line 305. The differential pitch between proximal threaded region 105 and distal threaded region 115 of compression screw 100 creates compression across fracture line 305 and reduces the fracture. With compression screw 100 thoroughly countersunk, k-wire 300 is removed. Next, internal retaining pin 200 is removed from compression screw 100, whereupon the strained (i.e., stretched) compression screw 100 will attempt to foreshorten to its pre-strained (i.e., pre-stretched) condition. Inasmuch as proximal threaded region 105 and distal threaded region 115 of compression screw 100 are disposed in bone fragments 310, 315, respectively, the foreshortening compression screw will further reduce the fracture if a gap exists, and generate and maintain additional compressive load across the fracture line 305, thereby enhancing healing.

As noted above, compression screw 100 is provided with a drive feature 130, whereby to turn compression screw 100 into bone. Drive feature 130 can be a standard screw drive feature such as a drive slot, a Philips (cruciform) drive configuration, a hex or hexalobe recess, or other engagement feature of the sort well known in the art.

As also noted above, internal retaining pin 200 is provided with a drive feature 220, whereby to advance internal retaining pin 200 into compression screw 100 or to remove internal retaining pin 200 from compression screw 100. While drive feature 220 is shown herein as comprising a hex recess, other drive features of the sort well known in the art may also be used.

In addition, as noted above, internal retaining pin 200 is preferably releasably secured to compression screw 100 via a screw mechanism (e.g., proximal screw thread 210 of internal retaining pin 200 engaging internal thread 175 of compression screw 100). However, if desired, other connection mechanisms (e.g., a bayonet mount) may be used to releasably connect internal retaining pin 200 to compression screw 100.

It should also be appreciated that compression screw system 5 need not be delivered over a k-wire. In this case, compression screw 100 and internal retaining pin 200 need not be fully cannulated.

In addition to the foregoing, in the preceding section, compression screw 100 is described as being strained (i.e., stretched) prior to the insertion of internal retaining pin 200 into the compression screw. However, if desired, internal retaining pin 200 can be inserted into compression screw 100 without compression screw 100 being pre-strained (i.e., without compression screw 100 being pre-stretched), in which case internal retaining pin 200 can be used to strain (i.e., stretch) compression screw 100, i.e., by virtue of the engagement of the advancing distal tip of internal retaining pin 200 with annular shoulder 165 of compression screw 100.

And in the foregoing description, compression screw 100 is described as being stretched while it is at a temperature below its austenite start temperature, and with the internal retaining pin being inserted into the compression screw while the compression screw is maintained below its austenite start temperature. However, if desired, compression screw 100 may be stretched while it is at a temperature above its austenite start temperature, whereby to create stress-induced martensite, with the internal retaining pin being inserted into the compression screw while the compression screw is maintained in its stretched condition.

If desired, compression screw system 5 may be deployed using two separate drivers, i.e., a first driver for deploying compression screw 100 into the bone and a second driver for removing internal retaining pin 200 from the deployed compression screw 100. However, if desired, a single two-part driver may be used, where one part of the two-part driver deploys the compression screw 100 into the bone and a second part of the two-part driver removes internal retaining pin 200 from the deployed compression screw 100.

By way of example but not limitation, and looking now at FIGS. 10A-10E, there is shown a two-part driver 500 which may be used to deploy compression screw 100. Two-part driver 500 comprises a first drive element 505 which is cannulated and includes fingers 510 at its distal end for engaging drive feature 130 in compression screw 100. Two-part driver 500 also includes a second drive element 515 which is sized to fit within the cannulation of first drive element 505 and comprises a hexagonal (or other non-circular) projection 520 configured to be received within drive feature 220 of internal retaining pin 200. In this form of the invention, second drive element 515 is loaded into first drive element 505 so that projection 520 of second drive element 515 sits adjacent to, but radially inboard, of fingers 510 of first drive element 505, the pre-strained compression screw 100 (carrying internal retaining pin 200 therein) is mated with two-part driver 500 so that fingers 510 of first drive element 505 mate with drive feature 130 of compression screw 100, and so that projection 520 of second drive element 515 mates with drive feature 220 of internal retaining pin 200. Then two-part driver 500 is used to install the pre-strained compression screw 100 (carrying internal retaining pin 200 therein) in bone, i.e., by first turning compression screw 100 with first drive element 505 so as to advance compression screw 100 into bone, and then turning second drive element 515 so as to withdraw internal retaining pin 200 from compression screw 100, whereby to permit compression screw 100 to foreshorten. It may be beneficial to hold first drive element 505 stationary while turning second drive element 515, so as not to "back-out" the compression screw 100 while loosening internal retaining pin 200.

It should be appreciated that with the compression screw system 5 shown in FIG. 1, internal retaining pin 200 is held in position relative to compression screw 100 by virtue of the engagement of proximal screw thread 210 of proximal threaded region 205 of internal retaining pin 200 with internal thread 175 of proximal counterbore 160 in compression screw 100.

In another form of the invention, internal retaining pin 200 can be incorporated as part of a single-use delivery device, where portions of the single-use delivery device engage compression screw 100 and hold compression screw 100 in its stretched condition until compression screw 100 is released from the delivery device, as will hereinafter be discussed in further detail. Preferably, in this form of the invention, compression screw 100 is provided pre-strained and pre-loaded onto the delivery device, which is preferably a single-use delivery device that may be disposable.

Figure 11:
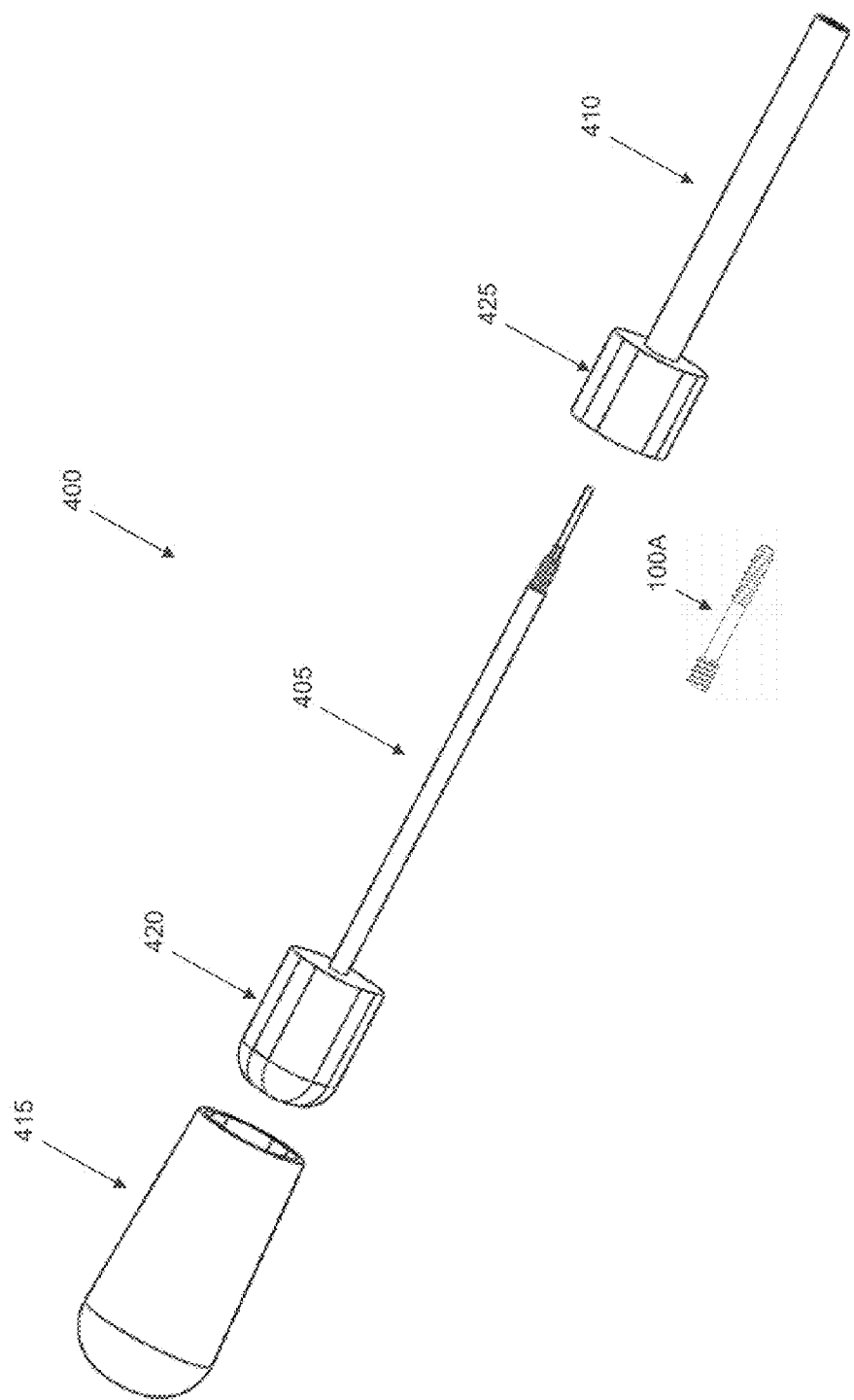
FIG. 11 is a schematic view showing another novel compression screw system formed in accordance with the present invention.

More particularly, and looking now at FIG. 11, there is shown a novel compression screw system 400 formed in accordance with the present invention. Novel compression screw system 400 comprises a compression screw 100A, a cannulated inner driver 405, a cannulated outer driver 410, and a coupling cap 415. Cannulated inner driver 405, cannulated outer driver 410, and coupling cap 415 essentially comprise a delivery device for delivering compression screw 100A to a fracture site as will hereinafter be discussed. Compression screw 100A is substantially the same as the compression screw 100 discussed above, except as will hereinafter be discussed. Pre-strained (e.g., stretched) compression screw 100A is slidably mounted to cannulated inner driver 405 and is selectively secured to cannulated inner driver 405 by cannulated outer driver 410, as will hereinafter be discussed. Cannulated outer driver 410 fits over cannulated inner driver 405, and coupling cap 415 fits over the drive handle 420 of cannulated inner driver 405 and over the drive handle 425 of cannulated outer driver 410. With coupling cap 415 installed, cannulated inner driver 405 and cannulated outer driver 410 may be rotated as a unit. When the coupling cap 415 is removed, cannulated outer driver 410 may be held stationary and cannulated inner driver 405 may be rotated independently of cannulated outer driver 410.

In one preferred form of the invention, compression screw 100A, cannulated inner driver 405, cannulated outer driver 410 and coupling cap 415 are provided in the form of a sterilized kit. The kit may include additional instruments to aid in the implantation of the screw (e.g., k-wire, drill bit, screw size guide, etc.).

Looking next at FIG. 12, compression screw 100A is substantially identical to compression screw 100 discussed above, except that proximal counterbore 160A of compression screw 100A (i) omits the internal screw thread 175 of compression screw 100, and (ii) comprises the drive feature 130A. To this end, proximal counterbore 160A comprises a non-circular cross-section (e.g., hexagonal, hexalobe, etc.). In one preferred form of the invention, proximal counterbore 160A has a hexagonal cross-section, whereby to provide the drive feature 130A.

Figure 15:
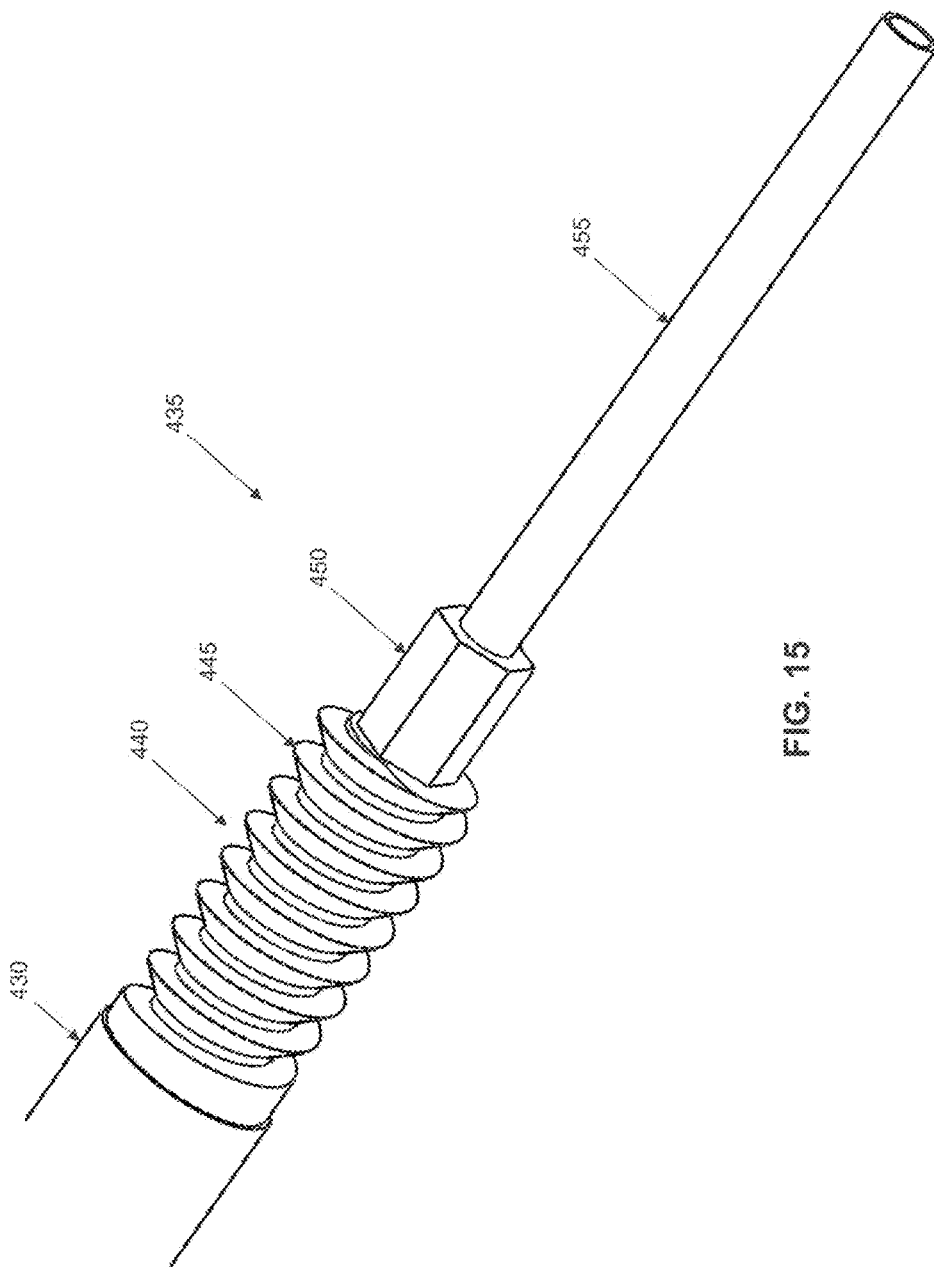

Cannulated inner driver 405 is shown in greater detail in FIGS. 13-15. Cannulated inner driver 405 comprises a shaft 430, a compression screw interface region 435 disposed at the distal end of shaft 430, and the aforementioned handle 420. Cannulated inner driver 405 is fully cannulated so as to allow cannulated inner driver 405 to be movably mounted on a k-wire, as will hereinafter be discussed.

Compression screw interface region 435 has a proximal threaded region 440 adjacent to the distal end of shaft 430. Proximal threaded region 440 comprises proximal thread 445 that has an identical pitch to proximal thread 110A of the proximal threaded region 105A of compression screw 100A. Compression screw interface region 435 also comprises a drive feature 450 which is disposed distal to proximal thread 445. Drive feature 450 is designed to interface with drive feature 130A on compression screw 100A. By way of example but not limitation, where drive feature 130A on compression screw 100A comprises a hex recess, drive feature 450 on compression screw interface region 435 comprises a hex driver (FIG. 15). A hollow distal cylindrical region 455 is disposed distal to drive feature 450. Hollow distal cylindrical region 455 is sized so that when drive feature 450 of compression screw interface region 435 is received in drive feature 130A of a pre-strained (i.e., pre-stretched) compression screw 100A, the distal end of hollow distal cylindrical region 455 abuts annular shoulder 165A of compression screw 100A.

Thus, in this form of the invention, compression screw interface region 435 provides a modified form of internal retaining pin for holding compression screw 100A in a stretched condition. However, inasmuch as drive feature 450 on compression screw interface region 435 does not lock, in a longitudinal sense, to drive feature 130A on compression screw 100A (although it does lock, in a rotational sense, to drive feature 130A on compression screw 100A), cannulated outer driver 410 is used to hold a strained (i.e., stressed) compression screw 100A in its strained (i.e., stretched) condition on compression screw interface region 435 until compression screw 100A is released from cannulated inner driver 405 and cannulated outer driver 410, as will hereinafter be discussed in further detail.

Looking next at FIGS. 16 and 17, cannulated outer driver 410 comprises the aforementioned drive handle 425 and a length of cannulated rod 460 extending distal to drive handle 425. Cannulated rod 460 comprises an internal thread 465 at its distal end. Internal thread 465 is sized to engage proximal thread 445 of compression screw interface region 435 of cannulated inner driver 405, and to engage proximal screw thread 110A of proximal threaded region 105A of compression screw 100A, whereby to allow cannulated outer driver 410 to be secured to cannulated inner driver 405 and to compression screw 100A and, by doing so, to selectively secure compression screw 100A to cannulated inner driver 405. Cannulated outer driver 410 comprises a bore 470 which receives shaft 430 of cannulated inner driver 405, and a bearing 475 can be pressed into bore 470 to allow cannulated inner driver 405 to make a close sliding fit inside cannulated outer driver 410.

Looking next at FIGS. 18-24, a strained (i.e., stretched) compression screw 100A is intended to be loaded onto compression screw interface region 435 of cannulated inner driver 405, and then selectively secured thereto by means of cannulated outer driver 410, until compression screw 100A is to be used to secure together bone fragments. More particularly, cannulated outer driver 410 is moved distally along cannulated inner driver 405 until internal thread 465 of cannulated outer driver 410 engages proximal thread 445 of cannulated inner driver 405 (FIGS. 18-20). Compression screw 100A is cooled below its austenite start temperature, more preferably below its martensite start temperature, and most preferably below its martensite finish temperature, and strained (i.e., stretched) using a stretching mechanism (not shown) of the sort which will be apparent to those skilled in the art in view of the present disclosure. While "cold" (i.e., at a temperature below its austenite start temperature, more preferably below its martensite start temperature, and most preferably below its martensite finish temperature), compression screw 100A is slid over hollow cylindrical region 455 of compression screw interface region 435 of cannulated inner driver 405 until drive feature 450 of cannulated inner driver 405 is received in drive feature 130A of compression screw 100A. See FIGS. 21-23. Then cannulated outer driver 410 is advanced distally along cannulated inner driver 405, and rotated, so that internal thread 465 of cannulated outer driver 410 engages proximal screw thread 110A of compression screw 100A. See FIG. 24. As this occurs, internal thread 465 of cannulated outer driver 410 remains in contact with proximal thread 445 of cannulated inner driver 405. Thus it will be seen that internal thread 465 of cannulated outer driver 410 simultaneously engages the proximal thread 445 of cannulated inner driver 405 and the proximal screw thread 110A of compression screw 100A. As a result, internal thread 465 of cannulated outer driver 410 effectively secures compression screw 100A to cannulated inner driver 405.

It will be appreciated that when compression screw 100A is secured to cannulated inner driver 405 by means of cannulated outer driver 410, the distal end of hollow cylindrical region 455 of cannulated inner driver 405 abuts annular shoulder 165A of compression screw 100A, so that compression screw 100A can be warmed to a temperature above its austenite start temperature without the compression screw shortening.

Looking next at FIGS. 25-28, compression screw 100A can be released from cannulated outer driver 410 and cannulated inner driver 405 by rotating cannulated inner driver so as to bring compression screw 100A distal to cannulated outer driver 410 (and hence disengage proximal screw thread 110A of compression screw 100A from internal thread 465 of cannulated outer driver 410). When this occurs, compression screw 100A will no longer be mechanically prevented from foreshortening (FIG. 27) and may longitudinally separate from cannulated inner driver 405 (FIG. 28).

Figure 29:
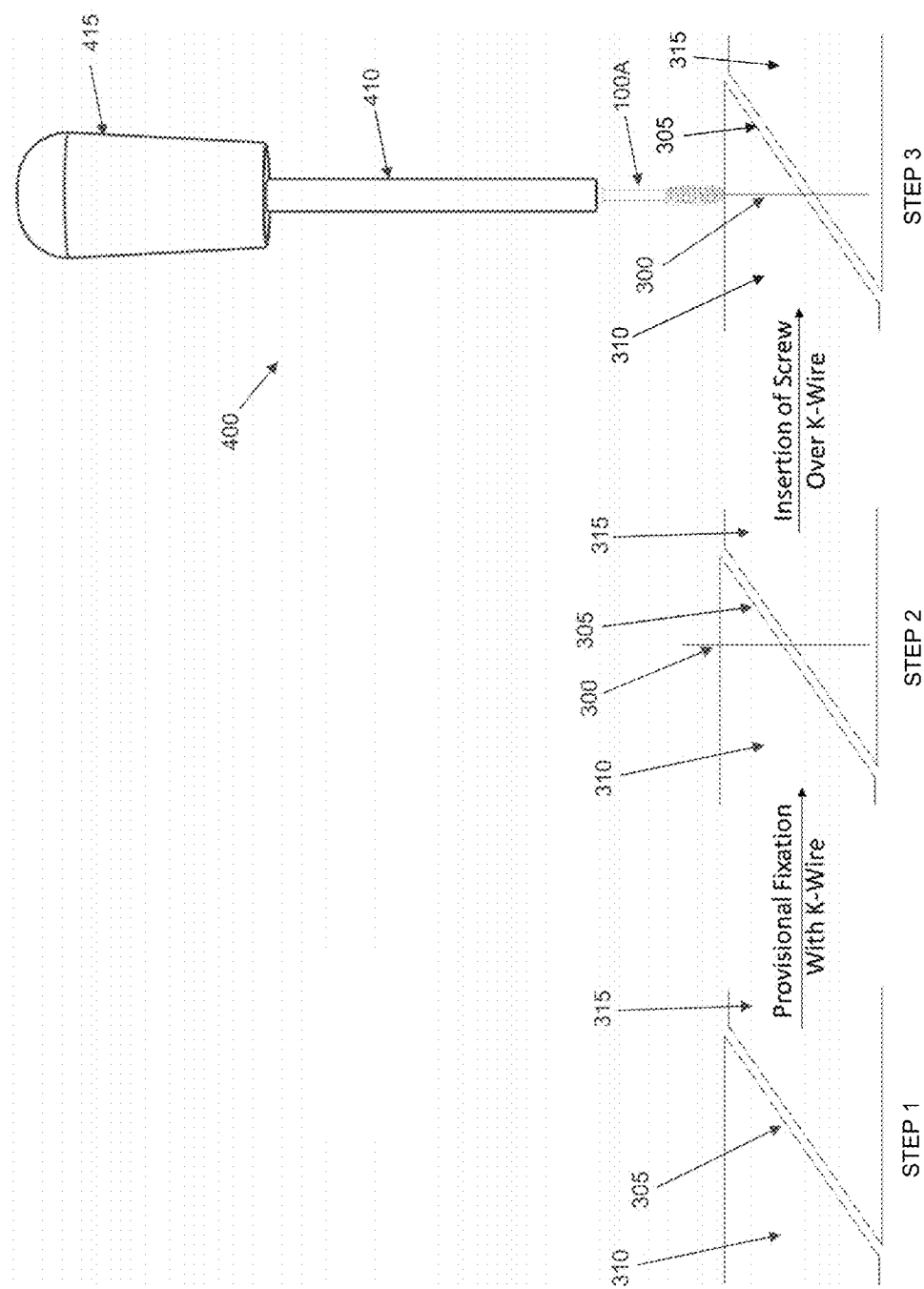

Compression screw system 400 can be used to aid in the healing of fractured bone, e.g., the scaphoid of the wrist, diaphysis of the fifth metatarsal, and the proximal interphalangeal joint of the second, third, fourth or fifth toe. More particularly, and looking now at FIGS. 29 and 30, a k-wire 300 is first inserted across a fracture line 305 to provisionally stabilize bone fragments 310, 315. Compression screw system 400, comprising the strained (i.e., stretched) compression screw 100A mounted on its delivery device (i.e., cannulated inner driver 405, cannulated outer driver 410 and coupling cap 415), is then slid over k-wire 300 and turned into the bone by turning coupling cap 415.

When the distal end of cannulated outer driver 410 contacts the cortical surface of bone fragment 310, the compression screw 100A can be turned further with cannulated outer driver 410 so as to reduce the fracture and generate compression between the bone fragments 310, 315. More particularly, when the cannulated outer driver 410 is turned further, compression screw 100A pulls the bone fragments further together (i.e., in the manner of a lag screw).

Thereafter, compression screw 100A is advanced out of cannulated outer driver 410 and further into the bone. To this end, coupling cap 415 is removed, and drive handle 425 of cannulated outer driver 410 is held stationary while drive handle 420 of cannulated inner driver 405 is turned, so that drive feature 450 of cannulated inner driver 405 turns drive feature 130A of compression screw 100A so as to advance compression screw 100A along internal thread 465 of cannulated outer driver 410 and further into the bone. This causes cannulated inner driver 405 to countersink compression screw 100A. As this occurs, the differential pitch between proximal screw thread 110A and distal screw thread 120A further reduces the fracture and generates further compression through the aforementioned differential thread pitch.

As compression screw 100A exits cannulated outer driver 410 and becomes thoroughly countersunk, compression screw 100A becomes disengaged from internal thread 465 of cannulated outer driver 410, thereby allowing compression screw 100A to attempt to foreshorten. Inasmuch as proximal threaded region 105A and distal threaded region 115A of compression screw 100A are disposed in bone fragments 310, 315, respectively, the compression screw will generate and maintain an additional compressive load across the fracture line 305 as the compression screw foreshortens, thereby enhancing healing.

It should be appreciated that compression screw system 400 need not be delivered over a k-wire. In this case, compression screw 100A, cannulated inner driver 405 and coupling cap 405 need not be fully cannulated.

In addition to the foregoing, in the preceding section, compression screw 100A is described as being strained (i.e., stretched) prior to being mounted to cannulated inner driver 405. However, if desired, compression screw 100A can be mounted to cannulated inner driver 100A without compression screw 100A being pre-strained (i.e., pre-stretched), in which case cannulated inner driver 405 can be used to strain (i.e., stretch) compression screw 100A, i.e., by virtue of the engagement of the distal tip of cannulated inner driver 405 with annular shoulder 165A of compression screw 100 when cannulated outer driver 410 engages compression screw 100A and pulls compression screw 100A proximally.

And in the foregoing description, compression screw 100A is described as being stretched while it is at a temperature below its austenite start temperature, and then being loaded onto the cannulated inner driver and locked into position (i.e., with the cannulated outer driver) while the compression screw is maintained below its austenite start temperature. However, if desired, compression screw 100A may be stretched while it is at a temperature above its austenite start temperature, whereby to create stress-induced martensite, and the compression screw mounted onto the cannulated inner driver and locked into position (i.e., with the cannulated outer driver) while the compression screw is maintained in its stretched condition.

Test Data

It has been reported that the "mean time to union" for a non-displaced scaphoid fracture is 6 to 8 weeks. At the time of insertion, nominally similar dimensioned conventional compression screws (between 3.0 and 3.6 mm distal major diameter), generate on average about 155 N of compressive force. Comparatively, the compression screw system of the present invention is capable of generating additional compression (for example, about 190 N) because of an increased thread pullout resistance.

Following the first 12 hours after implantation, compression decays on average by about 43% for conventional compression screws. For some conventional compression screws, that decay is as high as 55%. The compression screw system of the present invention loses only about 20% of its compression over a 12 hour period. This occurs as the bone relaxes and remodels around the threads. After this 12 hour period, a new steady state of compression of around 100 N or greater of compression is achieved and maintained, and correlates with the force generated by the novel compression screw as it recovers its strain in the hollow central bridge region. This compressive load is actively maintained until the novel compression screw has fully restored the strain. It should be appreciated that the force generated by the novel compression screw as it recovers can be modified for different bone qualities and indications by adjusting the parameters discussed above.

It should be noted that larger diameter compression screws of the present invention can generate and maintain greater compressive loads, and conversely, smaller diameter compression screws of the present invention will generate and maintain lesser compressive loads. Since the recovery force is a function of the cross-sectional area of the novel compression screw's central counterbore 145A, a cannulated 7.5 mm screw (distal major diameter) can generate and maintain about 400 N of force. Larger diameter compression screws of the present invention can support greater compressive loads since the threaded regions may be longer and/or deeper and thus have greater surface area to distribute the force over.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A compression screw system comprising:
   a compression screw comprising a shaft, a screw thread formed on said shaft at a distal location, and a bone-engaging feature formed on said shaft at a proximal location, at least a portion of said shaft disposed between said screw thread and said bone-engaging feature is capable of being stretched; and
   a holding element connectable to said compression screw for releasably holding said at least a portion of said shaft in a stretched condition, wherein said holding element comprises a locking feature for releasably locking said holding element to said compression screw so as to hold said at least a portion of said shaft in said stretched condition.

2. The compression screw system according to claim 1 wherein said bone-engaging feature comprises a screw head.

3. The compression screw system according to claim 1 wherein said compression screw comprises a shape memory material.

4. The compression screw system according to claim 1 wherein said holding element is configured to engage a shoulder in said compression screw when said locking feature locks said holding element to said compression screw.

5. A method for treating a fracture, said method comprising:
   longitudinally stretching a compression screw so that said compression screw is in a longitudinally stretched condition, wherein said compression screw is longitudinally stretched while said compression screw is maintained at a temperature below an austenite start temperature, wherein said compression screw comprises a shaft, a screw thread formed on said shaft at a distal location, and a bone-engaging feature formed on said shaft at a proximal location, at least a portion of said shaft disposed between said screw thread and said bone-engaging feature is capable of being stretched, a holding element connectable to said compression screw for releasably holding said at least a portion of said shaft in a stretched condition, and said compression screw comprises a shape memory material;
   holding said compression screw in the longitudinally stretched condition by releasably connecting said holding element to said compression screw;
   inserting said compression screw into bone while said compression screw is in the longitudinally stretched condition so that said compression screw extends across the fracture; and
   releasing said compression screw from the longitudinally stretched condition by disconnecting said holding element from said compression screw so as to apply compression across the fracture.

6. The method according to claim 5 wherein said bone-engaging feature comprises a screw head.

7. The method according to claim 5 wherein said compression screw comprises an opening extending into said compression screw, and further wherein said holding element is extendable into said opening.

8. A method for treating a fracture, said method comprising:
   longitudinally stretching a compression screw so that said compression screw is in a longitudinally stretched condition, wherein said compression screw comprises a shaft, a screw thread formed on said shaft at a distal location, and a bone-engaging feature formed on said shaft at a proximal location, at least a portion of said shaft disposed between said screw thread and said bone-engaging feature is capable of being stretched, a holding element is connectable to said compression screw for releasably holding said at least a portion of said shaft in a stretched condition, and said holding element comprises a locking feature for releasably locking said holding element to said compression screw;
   holding said compression screw in the longitudinally stretched condition by releasably connecting said holding element to said compression screw;

inserting said compression screw into bone while said compression screw is in the longitudinally stretched condition so that said compression screw extends across the fracture; and releasing said compression screw from the longitudinally stretched condition by disconnecting said holding element from said compression screw so as to apply compression across the fracture.

9. The method according to claim 8 wherein said holding element is configured to engage a shoulder in said compression screw when said locking feature locks said holding element to said compression screw.

10. A compression screw system, said compression screw system comprising:
a compression screw comprising a shaft capable of being stretched, said shaft having a proximal end, a distal end, and a lumen extending therebetween, said proximal end of said shaft comprising a proximal screw thread and said distal end of said shaft comprising a distal screw thread, said lumen comprising a distal bore, an intermediate counterbore communicating with said distal bore so as to define a first shoulder, and a proximal counterbore communicating with said intermediate counterbore so as to define a second shoulder, said proximal counterbore comprising a connection feature and said proximal end of said shaft comprising a drive feature for turning said compression screw; and
an internal retaining pin comprising a pin shaft having a proximal end, a distal end and a lumen extending therebetween, said proximal end of said pin shaft comprising a second connection feature configured to mate with said connection feature of said proximal counterbore of said compression screw, and said distal end of said pin shaft terminating in a distal end surface, said internal retaining pin comprising a pin drive feature for turning said internal retaining pin, and said internal retaining pin being sized such that, when said shaft of said compression screw is stretched, and when said internal retaining pin is inserted into said lumen of said compression screw such that said second connection feature of said internal retaining pin is engaged with said connection feature of said proximal counterbore of said compression screw and contacts said second shoulder of said compression screw, said distal end surface of said pin shaft engages said first shoulder of said compression screw, whereby to prevent foreshortening of the stretched compression screw.

11. The compression screw system according to claim 10 wherein said shaft comprises a shape memory material.

12. The compression screw system according to claim 11 wherein said shape memory material comprises Nitinol.

13. The compression screw system according to claim 10 wherein said connection feature of said compression screw comprises an internal screw thread and further wherein said second connection feature of said internal retaining pin comprises a proximal screw thread.

14. The compression screw system according to claim 10 wherein said proximal thread of said compression screw has more threads per inch than said distal thread of said compression screw.

15. The compression screw system according to claim 10 wherein said proximal thread of said compression screw and said distal thread of said compression screw mirror one another.

16. The compression screw system according to claim 10 wherein said drive feature of said compression screw comprises at least one selected from the group consisting of a slot, a cruciform recess, a hex recess, and a hexalobe recess.

17. The compression screw system according to claim 10 wherein said lumen of said internal retaining pin comprises a distal bore and a proximal counterbore communicating with said distal bore so as to define a pin shoulder.

18. The compression screw system according to claim 17 wherein said proximal counterbore of said internal retaining pin comprises said pin drive feature.

19. The compression screw system according to claim 17 wherein said proximal counterbore of said internal retaining pin comprises a non-circular cross-section.

20. The compression screw system according to claim 10 wherein said distal end of said shaft of said compression screw comprises a self-cutting feature.

21. The compression screw system according to claim 10 wherein said distal end of said shaft of said compression screw comprises a self-tapping feature.

22. The compression screw system according to claim 10 wherein said compression screw and said internal retaining pin are packaged as a sterilized kit.

23. The compression screw system according to claim 22 wherein said system is packaged with said shaft of said compression screw in a stretched condition and with said internal retaining pin holding said compression screw in the stretched condition.

24. A compression screw system, said compression screw system comprising:
a compression screw comprising a shaft capable of being stretched, said shaft having a proximal end, a distal end, and a lumen extending therebetween, said proximal end of said shaft comprising a proximal screw thread and said distal end of said shaft comprising a distal screw thread, said lumen comprising a distal bore, an intermediate counterbore communicating with said distal bore so as to define a first shoulder, and a proximal counterbore communicating with said intermediate counterbore so as to define a second shoulder, said proximal counterbore comprising a drive feature for turning said compression screw;
a cannulated inner driver comprising a shaft having a proximal end, a distal end, and a lumen extending therebetween, said distal end of said shaft comprising a compression screw interface comprising an interface shaft having a proximal end and a distal end, said proximal end of said interface shaft comprising a proximal screw thread matching said proximal screw thread of said compression screw, said distal end of said interface shaft terminating in a distal end surface, and said compression screw interface comprising an interface drive feature for engaging said drive feature of said compression screw, whereby to allow said cannulated inner driver to turn said compression screw;
a cannulated outer driver comprising a shaft having a proximal end, a distal end, and a lumen extending therebetween, said distal end of said shaft of said cannulated outer driver comprising an internal screw thread sized to mate with said proximal screw thread of said compression screw interface of said cannulated inner driver and said proximal screw thread of said compression screw; and
a coupling cap for selectively coupling said cannulated outer driver to said cannulated inner driver;
said compression screw interface of said cannulated inner driver being sized such that, when said shaft of said compression screw is stretched, and when said compression screw is mounted on said compression screw interface such that said interface shaft is inserted into said lumen of said compression screw such that said proximal screw thread of said compression screw is disposed adjacent to said proximal screw thread of said compression screw interface, said interface drive feature of said compression screw interface engages said drive feature of said compression screw and said distal end surface of said interface shaft engages said first shoulder of said compression screw, whereby to prevent foreshortening of said stretched compression screw.

25. The compression screw system according to claim 24 wherein said shaft comprises a shape memory material.

26. The compression screw system according to claim 25 wherein said shape memory material comprises Nitinol.

27. The compression screw system according to claim 24 wherein said proximal thread of said compression screw has more threads per inch than said distal thread of said compression screw.

28. The compression screw system according to claim 24 wherein said proximal thread of said compression screw and said distal thread of said compression screw mirror one another.

29. The compression screw system according to claim 24 wherein said drive feature of said compression screw comprises at least one selected from the group consisting of a slot, a cruciform recess, a hex recess, and a hexalobe recess.

30. The compression screw system according to claim 24 wherein said distal end of said shaft of said compression screw comprises a self-cutting feature.

31. The compression screw system according to claim 24 wherein said distal end of said shaft of said compression screw comprises a self-tapping feature.

32. The compression screw system according to claim 24 wherein said drive feature of said compression screw mates with said interface drive feature of said cannulated inner driver so as to allow said cannulated inner driver to turn said compression screw while allowing said compression screw to move longitudinally relative to said cannulated inner driver.

33. The compression screw system according to claim 24 wherein said compression screw, said cannulated inner driver, said cannulated outer driver, and said coupling cap are packaged as a sterilized kit.

34. The compression screw system according to claim 33 wherein said system is packaged with said shaft of said compression screw in a stretched condition and with said compression screw interface holding said compression screw in the stretched condition.

* * * * *